US009206154B2

(12) United States Patent
Gershengorn et al.

(10) Patent No.: US 9,206,154 B2
(45) Date of Patent: Dec. 8, 2015

(54) INVERSE AGONISTS AND NEUTRAL ANTAGONISTS FOR THE TSH RECEPTOR

(75) Inventors: Marvin Gershengorn, Washington, DC (US); Susanne Neumann, Bethesda, MD (US); Wenwei Huang, Rockville, MD (US); Craig J. Thomas, Gaithersburg, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/579,251

(22) PCT Filed: Apr. 8, 2011

(86) PCT No.: PCT/US2011/031752
§ 371 (c)(1),
(2), (4) Date: Aug. 15, 2012

(87) PCT Pub. No.: WO2011/127388
PCT Pub. Date: Oct. 13, 2011

(65) Prior Publication Data
US 2012/0315217 A1 Dec. 13, 2012

Related U.S. Application Data

(60) Provisional application No. 61/322,138, filed on Apr. 8, 2010.

(51) Int. Cl.
*C07D 401/06* (2006.01)
*A61K 31/517* (2006.01)
*C07D 239/91* (2006.01)
*C07D 405/06* (2006.01)

(52) U.S. Cl.
CPC .......... *C07D 401/06* (2013.01); *A61K 31/517* (2013.01); *C07D 239/91* (2013.01); *C07D 405/06* (2013.01)

(58) Field of Classification Search
CPC ... A61K 31/517; A61K 51/00; C07D 405/06; C07D 401/06
USPC ............ 544/283, 284, 266.2, 289; 514/266.2, 514/283, 284, 266.21
See application file for complete search history.

(56) References Cited

U.S. PATENT DOCUMENTS

| 6,087,115 A | 7/2000 | Gershengorn et al. |
| 6,403,305 B1 | 6/2002 | Gershengorn et al. |
| 6,924,295 B2 | 8/2005 | Tajima et al. |
| 7,220,864 B2 | 5/2007 | Tajima et al. |
| 7,223,767 B2 | 5/2007 | Clark et al. |
| 7,229,990 B2 | 6/2007 | Timmers et al. |
| 7,317,006 B2 | 1/2008 | Hanssen et al. |
| 7,375,109 B2 | 5/2008 | Hanssen et al. |
| 2005/0038052 A1 | 2/2005 | Clark et al. |
| 2005/0250824 A1 | 11/2005 | Tajima et al. |
| 2006/0025406 A1 | 2/2006 | Askew, Jr. et al. |
| 2006/0030573 A1 | 2/2006 | Boyce et al. |
| 2006/0052303 A1 | 3/2006 | Sampath et al. |
| 2006/0069106 A1 | 3/2006 | Fu et al. |
| 2006/0229324 A1 | 10/2006 | Itai et al. |
| 2008/0167329 A1 | 7/2008 | Barrow et al. |
| 2008/0293699 A1 | 11/2008 | Reed et al. |
| 2009/0163545 A1* | 6/2009 | Goldfarb ................ 514/312 |
| 2009/0203716 A1 | 8/2009 | Gershengorn et al. |
| 2011/0195018 A1 | 8/2011 | Gershengorn et al. |

FOREIGN PATENT DOCUMENTS

| EP | 1 354 879 | 12/2001 |
| WO | WO 2007/075906 | 12/2006 |
| WO | WO 2007/136776 | 11/2007 |
| WO | WO 2008/086730 | 1/2008 |
| WO | WO 2008/153760 | 12/2008 |
| WO | WO2010/047674 | 4/2010 |

OTHER PUBLICATIONS

Wolff et al (1997).*
Banker et al (1997).*
Neuman et al., "Small molecule agonists . . . ", Proceedings of the National Acad. of Scie of the USA. (2009) vol. 106., No. 30, pp. 12471-12476.*
Non-Final Office Action from corresponding U.S. Appl. No. 13/125,045 dated Jan. 9, 2013.
Abe et al., "TSH is a Negative Regulator of Skeletal Remodeling," *Cell* 115:151-162, Oct. 17, 2003.
Jäschke et al., "A Low Molecular Weight Agonist Signals by Binding to Transmembrane Domain of Thyroid-stimulating Hormone Receptor (TSHR) and Luteinizing Hormone/Chorionic Gonadotropin Receptor (LHCGR)," *Journal of Biological Chemistry* 281(15):9841-9844, Apr. 14, 2006.
Martini et al., "The Effects of Recombinant TSH on Bone Turnover Markers and Serum Osteoprotegerin and RANKL Levels," *Thyroid* 18(4):455-460, 2008.
Moore et al., "Evaluation of Small-Molecular Modulators of the Luteinizing Hormone/Choriogonadotropin and Thyroid Stimulating Hormone Receptors: Structure—Activity Relationships and Selective Binding Patterns," *Journal of Medicinal Chemistry* 49:3888-3896, 2006 (Published online May 24, 2006).
Neumann et al., "A low-molecular-weight antagonist for the human thyrotropin receptor with therapeutic potential for hyperthyroidism," *Endocrinology* 149(12):5945-5950, Dec. 2008 (available online Jan. 31, 2008).
Neumann et al., "A New Small-Molecule Antagonist Inhibits Graves' Disease Antibody Activation of the TSH Receptor," *J Clin Endocrin Metab*. 96(2):0000-0000, Feb. 2011 (available online Dec. 2010).

(Continued)

Primary Examiner — Paul V Ward
(74) Attorney, Agent, or Firm — Klarquist Sparkman, LLP

(57) ABSTRACT

TSHR inverse agonists and neutral antagonists that are useful for treating Graves' orbitopathy, Graves' hyperthyroidism and/or thyroid cancer.

61 Claims, 18 Drawing Sheets

(56) References Cited

OTHER PUBLICATIONS

Neumann et al., "A Small Molecule Inverse Agonist for the Human Thyroid-Stimulating Hormone Receptor," *Endocrinology* 151(7):3454-3459, Jul. 2010.

Neumann et al., "Human TSH receptor ligands as pharmacological probes with potential clinical application," *Expert Rev. Endocrinol. Metab* 4(6):669, Nov. 1, 2009.

Neumann et al., "Small-molecule agonists for the thyrotropin receptor stimulate thyroid function in human thyrocytes and mice," *PNAS* 106(30):12471-12476, Jul. 28, 2009.

Sun et al., "Intermittent recombinant TSH injections prevent ovariectomy-induced bone loss," *PNAS* 105(11):4289-4294, Mar. 18, 2008.

Titus et al., "Quantitative High-Throughput Screening Using a Live-Cell cAMP Assay Identifies Small-Molecule Agonists of the TSH Receptor," *Journal of Biomolecular Screening* 13(2):120-127, Feb. 2008 (Published online Jan. 23, 2008).

"Drug-like compound stops thyroid overstimulation in early NIH studies," *NIH News* Dec. 1, 2010.

International Search Report from International PCT Application No. PCT/US2011/031752, dated Dec. 19, 2011.

International Search Report from PCT Application No. PCT/US2008/011958 dated Jul. 16, 2009.

Written Opinion of the International Searching Authority from International PCT Application No. PCT/US2011/031752, dated Dec. 19, 2011.

Written Opinion of the International Searching Authority from PCT Application No. PCT/US2008/011958 dated Jul. 16, 2009.

PubChem Compound Summary—CID 16759579; Create Date Nov. 9, 2007.

PubChem Compound Summary—CID 17757102; Create Date Nov. 30, 2007.

PubChem Compound Summary—CID 17757314; Create Date Nov. 30, 2007.

PubChem Compound Summary—CID 2887926; Create Date Jul. 29, 2005.

PubChem Compound Summary—CID 661788; Create Date Jun. 29, 2005.

Chen et al., "Identification of Key Amino Acid Residues in a Thyrotropin Receptor Monoclonal Antibody Epitope Provides Insight into Its Inverse Agonist and Antagonist Properties," *Endocrinology*, 149(7): 3427-3434, Apr. 3, 2008.

Chen et al. "A Monoclonal Antibody with Thyrotropin (TSH) Receptor Inverse Agonist and TSH Antagonist Activities Binds to the Receptor Hinge Region as Well as to the Leucine-Rich Domain," *Endocrinology*, 150(7):3401-3408, Jul. 2009.

\* cited by examiner

Basal Signaling

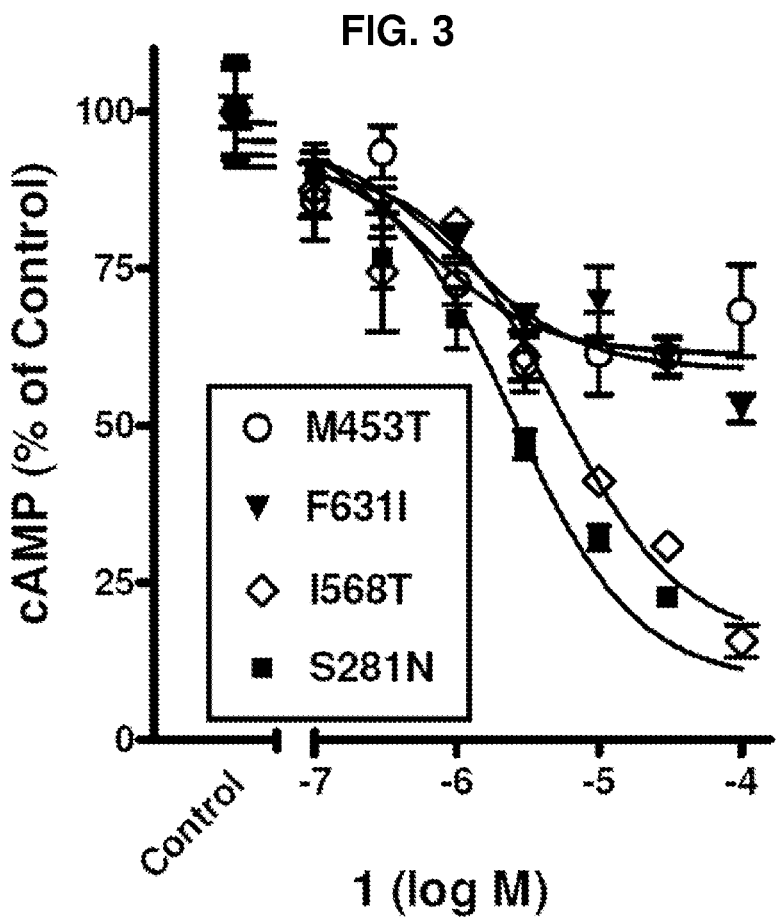
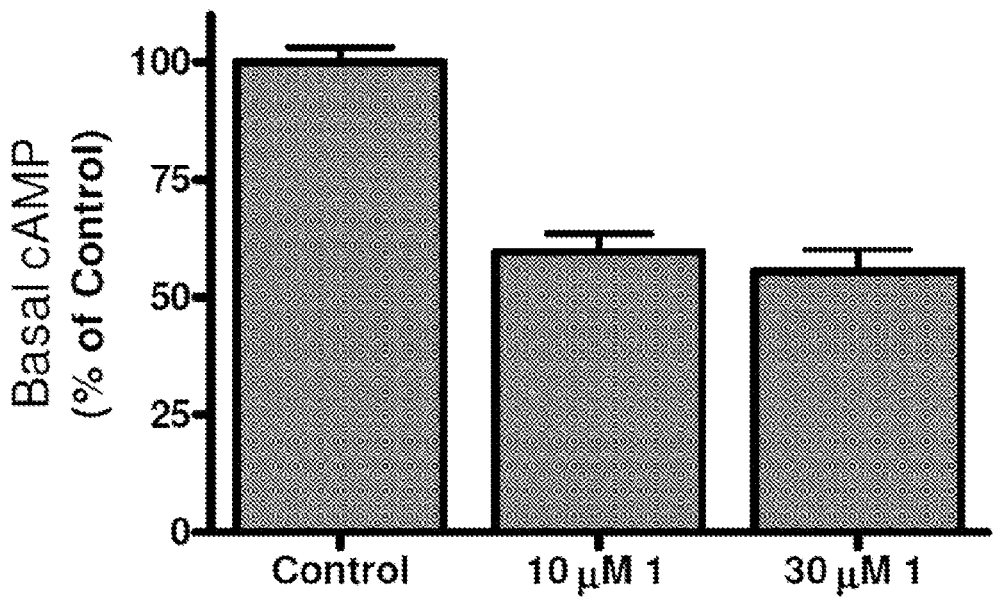

FIG. 5 (Page 1 of 3)
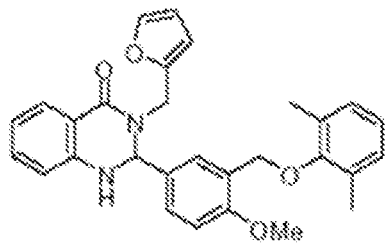
S2 (NCGC00161856)
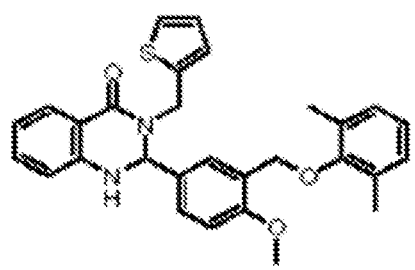
S2-1 (NCGC00229595)
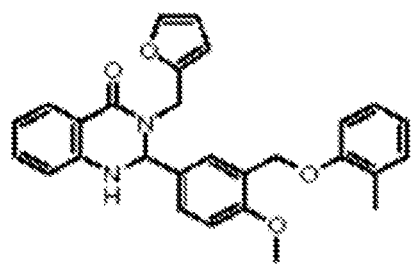
S2-2 (NCGC00229596)
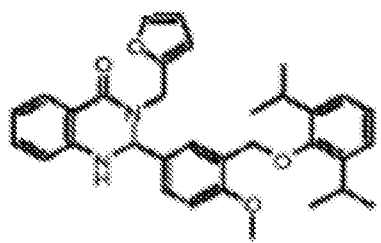
S2-3
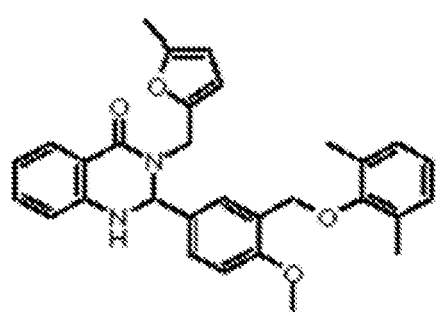
S2-4 (NCGC00229598)

FIG. 5 (Page 2 of 3)
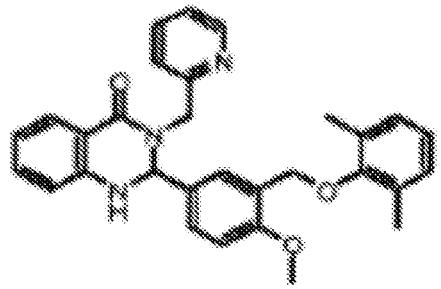
S2-5
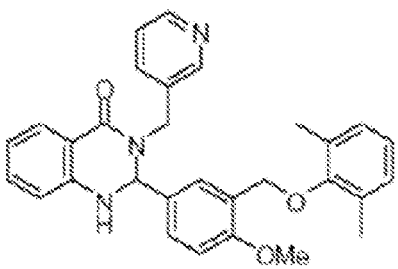
S2-6 (NCGC00229600)
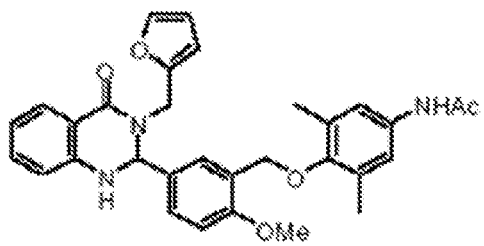
S2-7 (NCGC00242364)
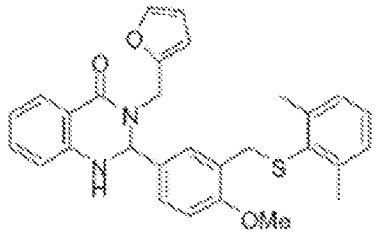
S2-8 (NCGC00242595)
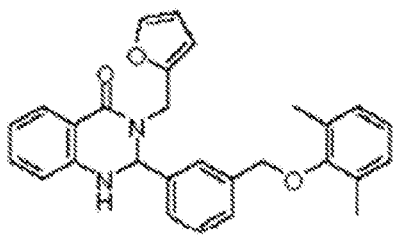
S2-9 (NCGC00229601)

FIG. 5 (Page 3 of 3)
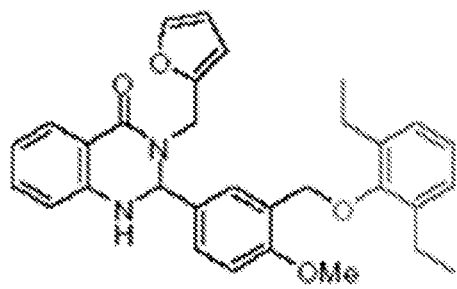
S2-10 (NCGC00229602)
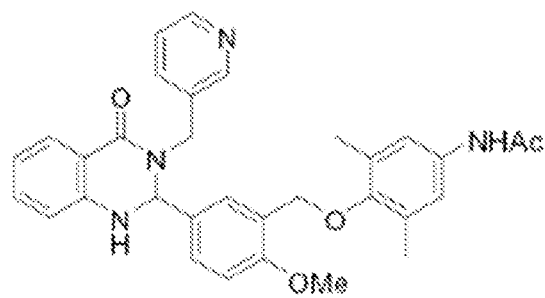
S2-17 (NCGC00242589-01)
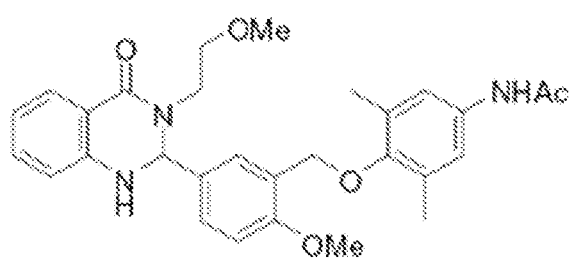
S2-29 (NCGC00242580

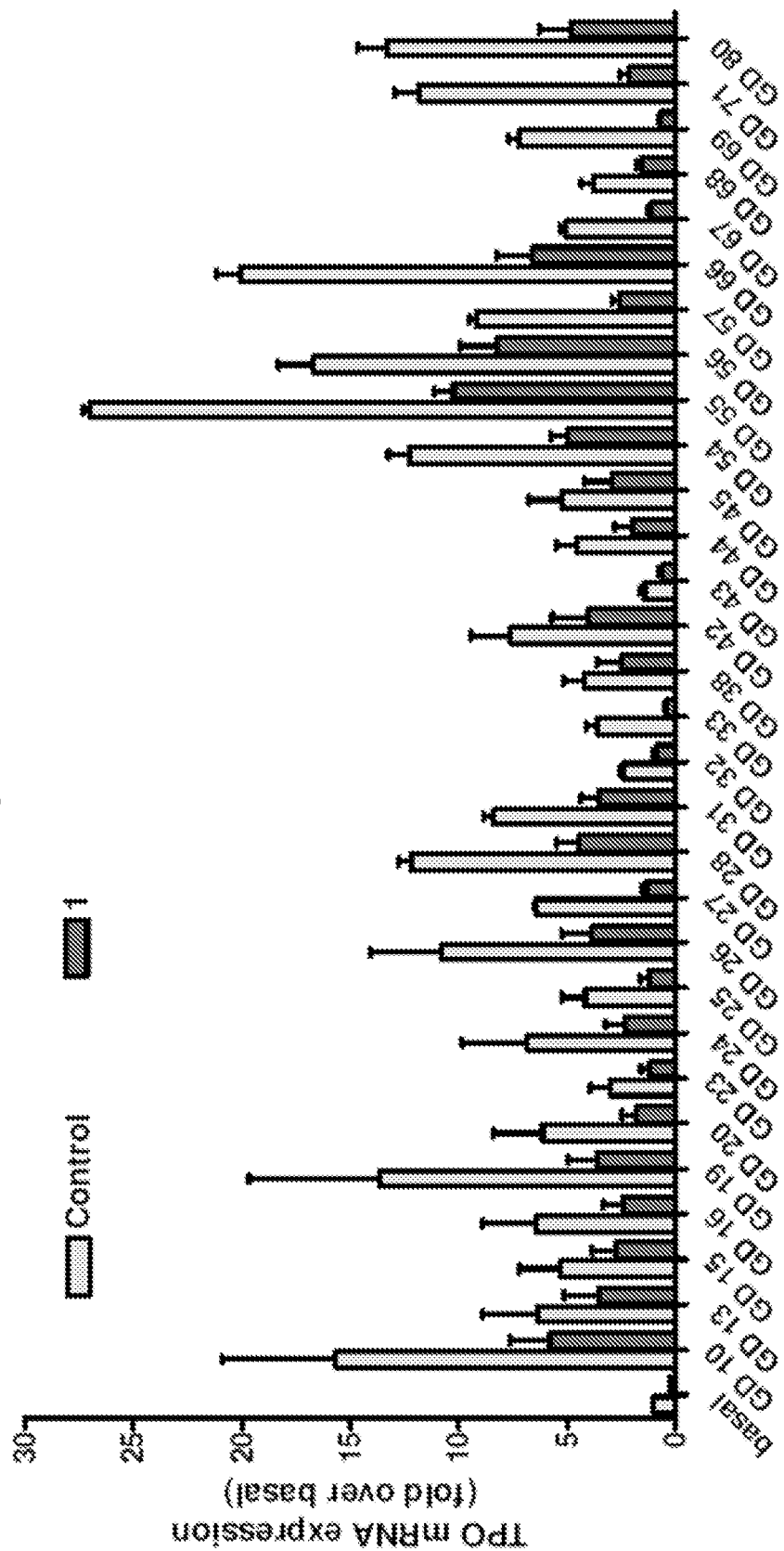

FIG. 15

| No | NCGC ID | SID | CID | R1, R3, Y | R2 | R4 | IC50 (uM) (TSHR) | Efficacy (TSHR) | IC50 (uM) (LHR) | Efficacy (LHR) | IC50 (uM) (FSHR) | Efficacy (FSHR) | IC50 (uM) (TSHR) (basal signal) | Efficacy (TSHR) (basal signal) |
|---|---|---|---|---|---|---|---|---|---|---|---|---|---|---|
| 1 | 161846 | 103967249 | 26879226 | H, MeO, O | furan | 2,6-dimethyl | 0.8 | 86% | 0.46 | 90% | 4.6 | 90% | 3 | 58% |
| 2 | 229631 | 103967266 | 50897601 | H, H, O | furan | 2,6-dimethyl | 1.3 | 88% | inactive | n.d. | 6.2 | 80% | 5 | 70% |
| 3 | 242364 | 103967290 | 50897609 | H, MeO, O | furan | 2,6-dimethyl-4-NHAc | 2.9 | 73% | inactive | n.d. | > 5.6 | 25% | 6 | 62% |
| 4 | 229600 | 103967285 | 50897816 | H, MeO, O | pyridine | 2,6-dimethyl | 3.5 | 58% | inactive | n.d. | 32.7 | 55% | 7 | 58% |
| 5 | 242535 | 103967318 | 50897794 | H, MeO, S | furan | 2,6-dimethyl | 9.9 | 51% | inactive | n.d. | 14.6 | 50% | neutral antagonist | n.d. |
| 6 | 229602 | 103967287 | 50897791 | H, MeO, O | furan | 2,6-diethyl | 22.9 | 44% | inactive | n.d. | > 3.7 | 32% | 11 | 30% |
| 7 | 229595 | 103967269 | 50897786 | H, MeO, O | thiophene | 2,6-dimethyl | >0.7 | 27% | n.d. | n.d. | n.d. | n.d. | partial agonist | n.d. |
| 8 | 229593 | 103967283 | 50897785 | H, MeO, O | furan | 2,6-dimethyl | 2.3 | 33% | inactive | n.d. | n.d. | n.d. | neutral antagonist | n.d. |
| 11 | 229596 | 103967281 | 50897769 | H, MeO, O | furan | 2-methyl | no antagonism | n.d. | n.d. | n.d. | n.d. | n.d. | agonist | n.d. |

INVERSE AGONISTS AND NEUTRAL ANTAGONISTS FOR THE TSH RECEPTOR

CROSS REFERENCE TO RELATED APPLICATIONS

This is the U.S. National Stage of International Application No. PCT/US2011/031752, filed Apr. 8, 2011, which was published in English under PCT Article 21(2), which in turn claims the benefit of U.S. Provisional Application No. 61/322,138, filed Apr. 8, 2010. The provisional application is incorporated herein in its entirety.

This application claims the benefit of U.S. Provisional Application No. 61/322,138, filed Apr. 8, 2010.

FIELD

Disclosed herein are compounds that are thyroid stimulating hormone receptor (TSHR) inverse agonists and neutral antagonists for diagnostic, analytical and therapeutic purposes.

BACKGROUND

Thyroid-stimulating hormone (TSH) is a heterodimeric glycoprotein hormone that regulates thyroid homeostasis by regulating the growth, proliferation and function of thyroid follicular cells. Cellular responses to TSH are mediated via the TSH receptor (TSHR) which is a distinct seven transmembrane-spanning receptor. TSHR is the major regulator of thyroid gland function and is expressed in tissues other than the thyroid including adipocyte (fat) precursor cells, adipocytes, fibroblasts, immune cells and bone. Activation of TSHR by its endogenous hormone TSH is required for normal thyroid homeostasis but may also regulate the function of these other tissues/cells.

TSHR is involved in the pathogenesis of several diseases. In Graves' disease, TSHR-stimulating antibodies (TSAbs) activate TSHR, mimicking the effects of TSH. This results in hyperthyroidism by activating TSHRs on thyroid cells and in Graves' orbitopathy (or ophthalmopathy or thyroid eye disease) by activating TSHRs on cells in the retro-orbital space behind the eyes. TSH also stimulates the growth, proliferation and metastasis of thyroid cancer cells by activating TSHRs on cancer cells. Indeed, most patients after surgery for thyroid cancer are treated with thyroid hormone to suppress TSH levels in the blood. TSHR exhibits basal signaling activity, that is, signaling activity in the absence of TSH or TSAbs.

SUMMARY

In one embodiment, there is disclosed herein a compound, or a pharmaceutically acceptable salt or ester thereof, having a structure of:

(Formula I)

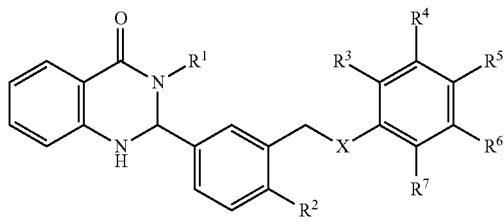

wherein $R^1$ is selected from a furanyl-containing group, a pyridinyl-containing group, a thienyl-containing group, hydroxyalkyl, or alkoxyalkyl;
$R^2$ is H, alkoxy, alkyl, substituted alkyl or halogen; and
$R^3$-$R^7$ are each individually selected from H, alkyl, substituted alkyl, halogen, or aminocarbonyl, provided that at least one of $R^3$ or $R^7$ is not H; and
X is O or S; provided that the compound is not

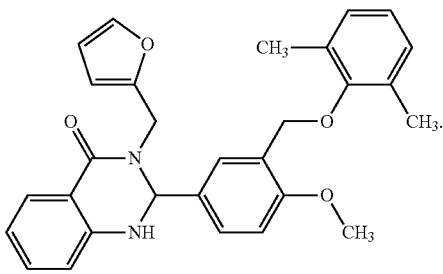

Also disclosed is a pharmaceutical composition comprising at least one pharmaceutically acceptable additive and a therapeutically effective amount of at least one compound, or a pharmaceutically acceptable salt or ester thereof, having a structure of:

(Formula I)

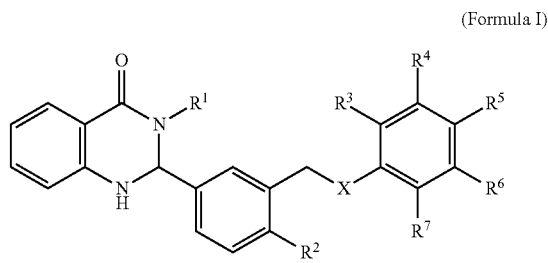

wherein $R^1$ is selected from a furanyl-containing group, a pyridinyl-containing group, a thienyl-containing group, hydroxyalkyl, or alkoxyalkyl;
$R^2$ is H, alkoxy, alkyl, substituted alkyl or halogen; and
$R^3$-$R^7$ are each individually selected from H, alkyl, substituted alkyl, halogen, or aminocarbonyl, provided that at least one of $R^3$ or $R^7$ is not H; and
X is O or S.

According to an additional embodiment disclosed herein, there is provided a method for making a pharmaceutical composition comprising combining at least one pharmaceutically acceptable additive and a therapeutically effective amount of at least one compound, or a pharmaceutically acceptable salt or ester thereof, having a structure of:

(Formula I)

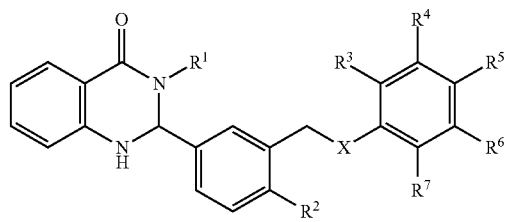

wherein R¹ is selected from a furanyl-containing group, a pyridinyl-containing group, a thienyl-containing group, hydroxyalkyl, or alkoxyalkyl;
R² is H, alkoxy, alkyl, substituted alkyl or halogen; and
R³-R⁷ are each individually selected from H, alkyl, substituted alkyl, halogen, or aminocarbonyl, provided that at least one of R³ or R⁷ is not H; and
X is O or S.

Also disclosed herein is a method of treating Graves' disease in a subject, comprising administering to the subject an inverse agonist of TSHR or a neutral antagonist of TSHR.

An additional embodiment disclosed herein is a method of treating thyroid cancer in a subject, comprising administering to the subject an inverse agonist of TSHR or a neutral antagonist of TSHR.

In a further embodiment disclosed herein, there is provided a method of treating Graves' disease in a subject, comprising administering to the subject a therapeutically effective amount of at least one compound, or a pharmaceutically acceptable salt or ester thereof, having a structure of:

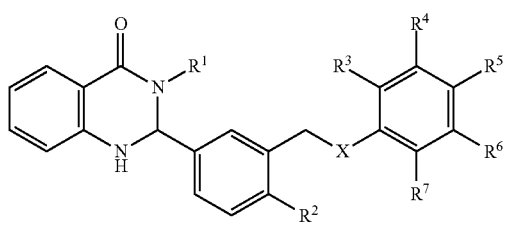

(Formula I)

wherein R¹ is selected from a furanyl-containing group, a pyridinyl-containing group, a thienyl-containing group, hydroxyalkyl, or alkoxyalkyl;
R² is H, alkoxy, alkyl, substituted alkyl or halogen; and
R³-R⁷ are each individually selected from H, alkyl, substituted alkyl, halogen, or aminocarbonyl; and
X is O or S.

In another embodiment disclosed herein, there is provided a method for inhibiting signaling stimulated by thyroid-stimulating antibodies (TSAbs) in a subject, comprising administering to the subject a therapeutically effective amount of at least one compound, or a pharmaceutically acceptable salt or ester thereof, having a structure of:

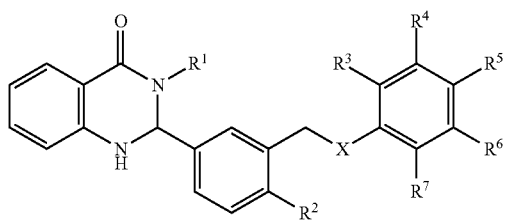

(Formula I)

wherein R¹ is selected from a furanyl-containing group, a pyridinyl-containing group, a thienyl-containing group, hydroxyalkyl, or alkoxyalkyl;
R² is H, alkyl, substituted alkyl or halogen; and
R³-R⁷ are each individually selected from H, alkyl, substituted alkyl, halogen, or aminocarbonyl; and
X is O or S.

According to a further embodiment disclosed herein, there is provided a method of treating hyperthyroidism in a subject, comprising administering to the subject a therapeutically effective amount of at least one compound, or a pharmaceutically acceptable salt or ester thereof, having a structure of:

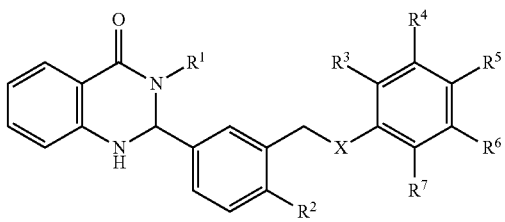

(Formula I)

wherein R¹ is selected from a furanyl-containing group, a pyridinyl-containing group, a thienyl-containing group, hydroxyalkyl, or alkoxyalkyl;
R² is H, alkoxy, alkyl, substituted alkyl or halogen; and
R³-R⁷ are each individually selected from H, alkyl, substituted alkyl, halogen, or aminocarbonyl; and
X is O or S.

Also disclosed herein is a method of treating thyroid cancer in a subject, comprising administering to the subject a therapeutically effective amount of at least one compound, or a pharmaceutically acceptable salt or ester thereof, having a structure of:

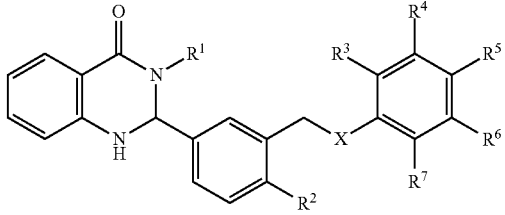

(Formula I)

wherein R¹ is selected from a furanyl-containing group, a pyridinyl-containing group, a thienyl-containing group, hydroxyalkyl, or alkoxyalkyl;
R² is H, alkoxy, alkyl, substituted alkyl or halogen; and
R³-R⁷ are each individually selected from H, alkyl, substituted alkyl, halogen, or aminocarbonyl, provided that at least one of R³ or R⁷ is not H; and
X is O or S.

In a further embodiment, disclosed herein is a method of treating thyroid cancer in a subject, comprising administering to the subject a therapeutically effective amount of at least one compound, or a pharmaceutically acceptable salt or ester thereof, having a structure of:

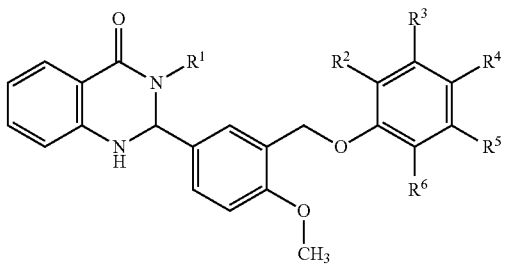

(Formula II)

wherein $R^1$ is selected from:

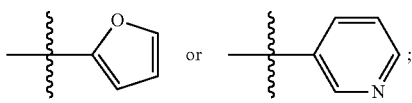

and $R^2$-$R^6$ are each individually selected from H, alkyl, substituted alkyl or halogen.

In a further embodiment, there is disclosed a method of treating hyperthyroidism in a subject, comprising administering to the subject a therapeutically effective amount of at least one compound, or a pharmaceutically acceptable salt or ester thereof, having a structure of:

(Formula II)

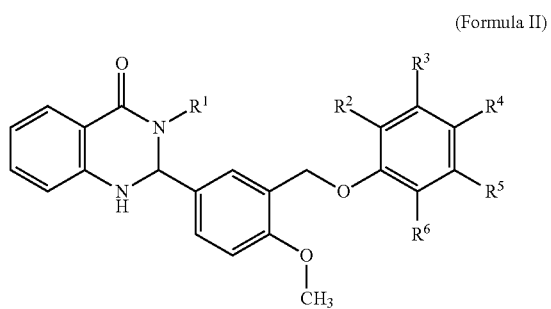

wherein $R^1$ is selected from:

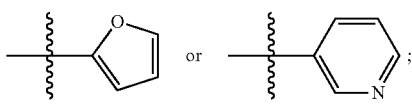

and $R^2$-$R^6$ are each individually selected from H, alkyl, substituted alkyl or halogen.

Also disclosed is a pharmaceutical composition comprising at least one pharmaceutically acceptable additive and a therapeutically effective amount of at least one compound, or a pharmaceutically acceptable salt or ester thereof, having a structure of:

(Formula II)

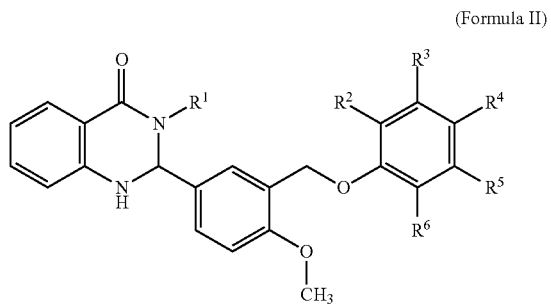

wherein $R^1$ is selected from:

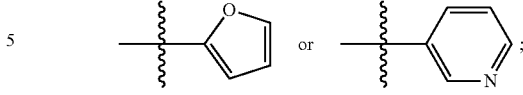

and $R^2$-$R^6$ are each individually selected from H, alkyl, substituted alkyl or halogen.

The foregoing will become more apparent from the following detailed description, which proceeds with reference to the accompanying figures.

BRIEF DESCRIPTION OF THE DRAWINGS

FIG. 1A) Chemical structure of 1 (2-(3-((2,6-dimethylphenoxy)methyl)-4-methoxyphenyl)-3-(furan-2-ylmethyl)-2,3-dihydroquinazolin-4(1H)-one) [NCGC00161856].

FIG. 1B) Cells stably expressing TSHRs were exposed to the noted concentrations of compound 1 for 40 min in HBSS and then for 60 min in HBSS+1 mM IBMX (Basal Signaling) as described in the Methods section below. After 60 min, the cells were lysed and cAMP levels were measured by ELISA. The data from two independent experiments with duplicate samples are shown as % of Control.

FIG. 2A) Cells stably expressing TSHRs were exposed to the noted concentrations of 1 20 min prior to the addition of a half-maximally effective concentration of TSH (2 nM) and 1 mM IBMX.

FIG. 2B) Cells stably expressing TSHRs were incubated in the absence of 1 or in the presence of 3, 10 or 30 µM 1 that was added 20 min prior to the addition various concentrations of TSH and 1 mM IBMX.

After 60 min, the cells were lysed and cAMP levels were measured by ELISA. The data from two independent experiments with duplicate samples are shown as % of Control. A Schild plot of these data was linear with a slope not different from 1.0 (not shown).

FIG. 3. Compound 1 inhibits the basal activities of constitutively active mutant TSHRs (CAMs). Cells transiently expressing mutant TSHRs—S281N, M453T, I568T or F631T—were incubated with the noted concentrations of 1 for xx min+1 mM IBMX. After 60 min, cAMP levels were measured by ELISA. The Control activities of the CAMs were: S281N—15±3.3-fold; M453T—27±7.3-fold; I568T—24±0.71-fold; and F6311-20±4.5-fold above Control. The data from two independent experiments with duplicate samples are shown as % of Control activities.

Figure 4B:
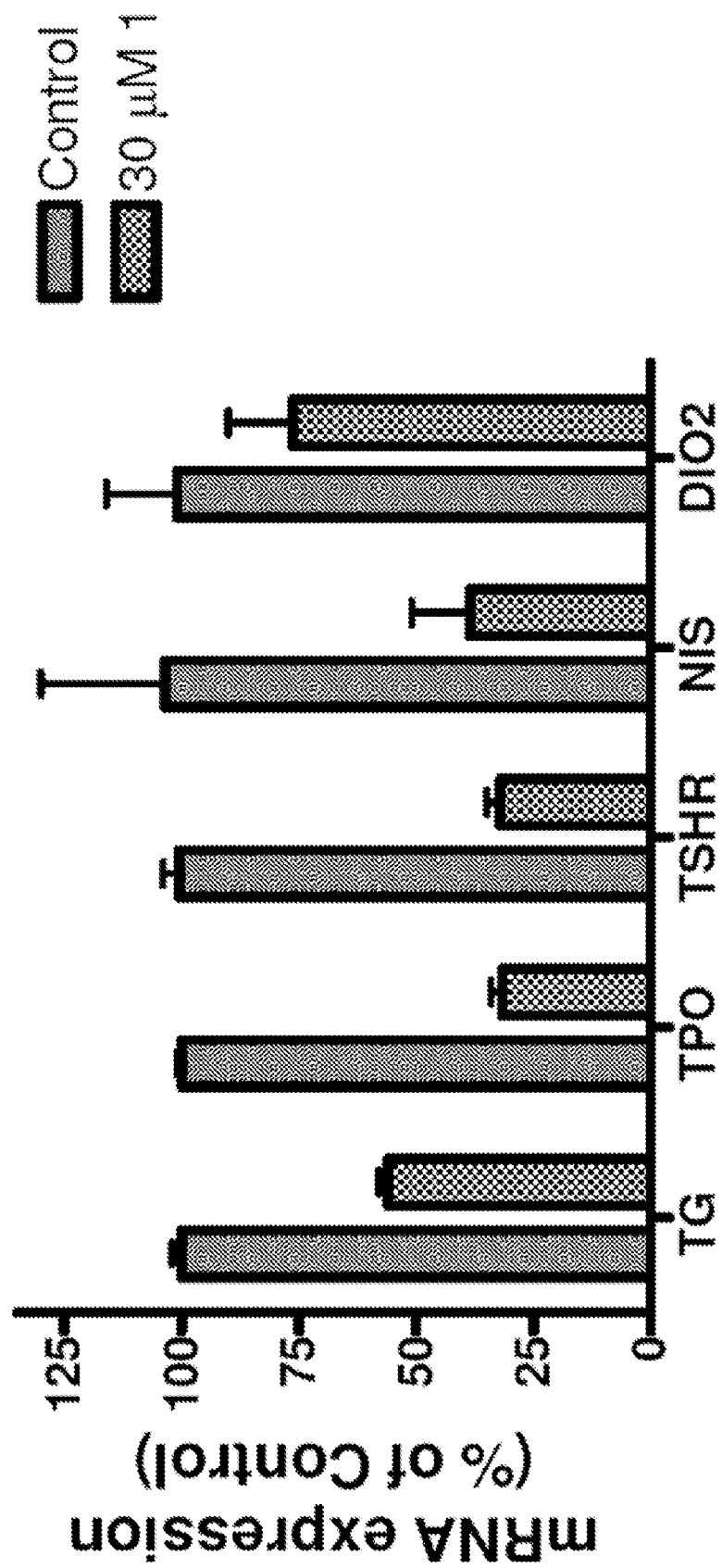

FIGS. 4A and 4B. Inhibition of basal cAMP production and of basal expression of mRNAs for TPO (thyroperoxidase), TSHR, TG (thyroglobulin), DIO2 (deiodinase type 2), and NIS (sodium-iodide symporter) by compound 1 in primary cultures of human thyrocytes.

FIG. 4A) Thyrocytes were incubated in HBSS/HEPES without or with 1 mM IBMX and without or with 1 for 2 hr at 37C. Thereafter, the buffers were aspirated, the cells lysed and intracellular cAMP was measured.

FIG. 4B) Thyrocytes were incubated in media containing 2% fetal bovine serum and 1 mM IBMX without or with 30 µM 1 as described in Methods. After 48 h, the cells were lysed and the levels of the mRNAs were measured and normalized to GAPDH mRNA. The mRNA levels are presented as fold stimulation over control. The data are from three independent experiments with duplicate samples are shown.

FIG. 5 is a list of compounds tested for TSHR inverse agonist activity and antagonist activity.

Figure 6:
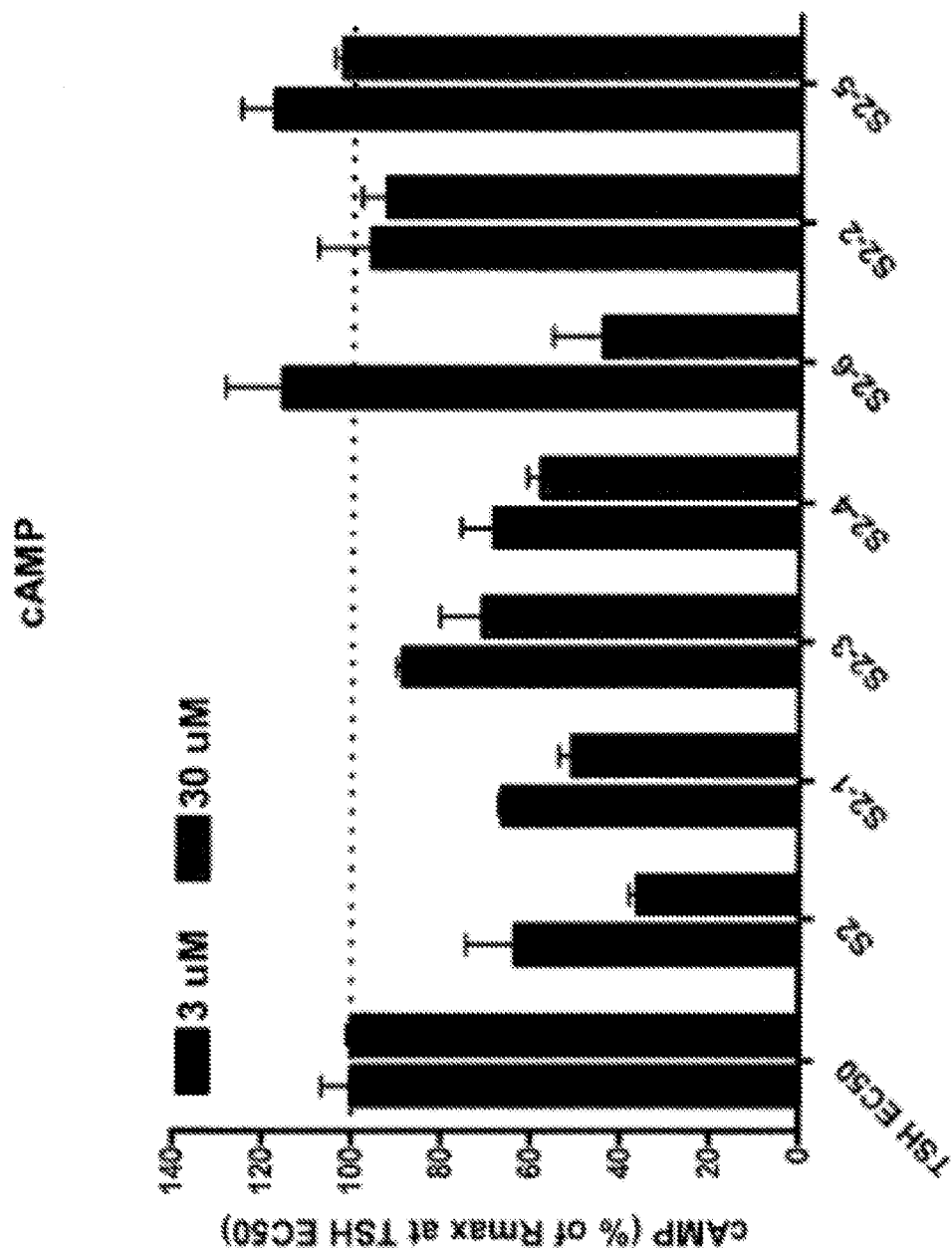

FIG. 6 is a graph showing the TSHR antagonist activity of several compounds. Compound S2 in FIG. 6 is the same compound as compound 1 described below.

Figure 7:
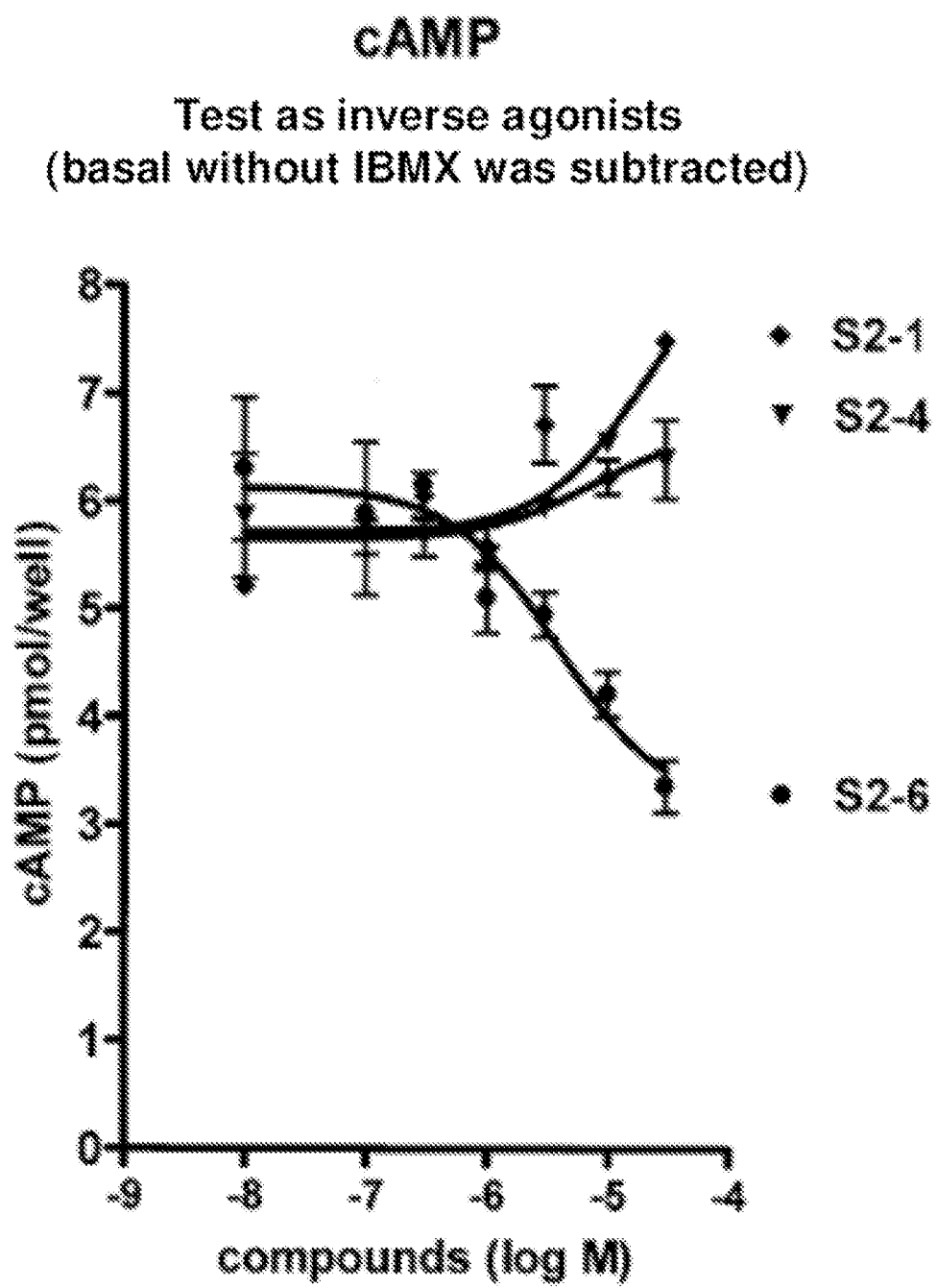
Figure 8:
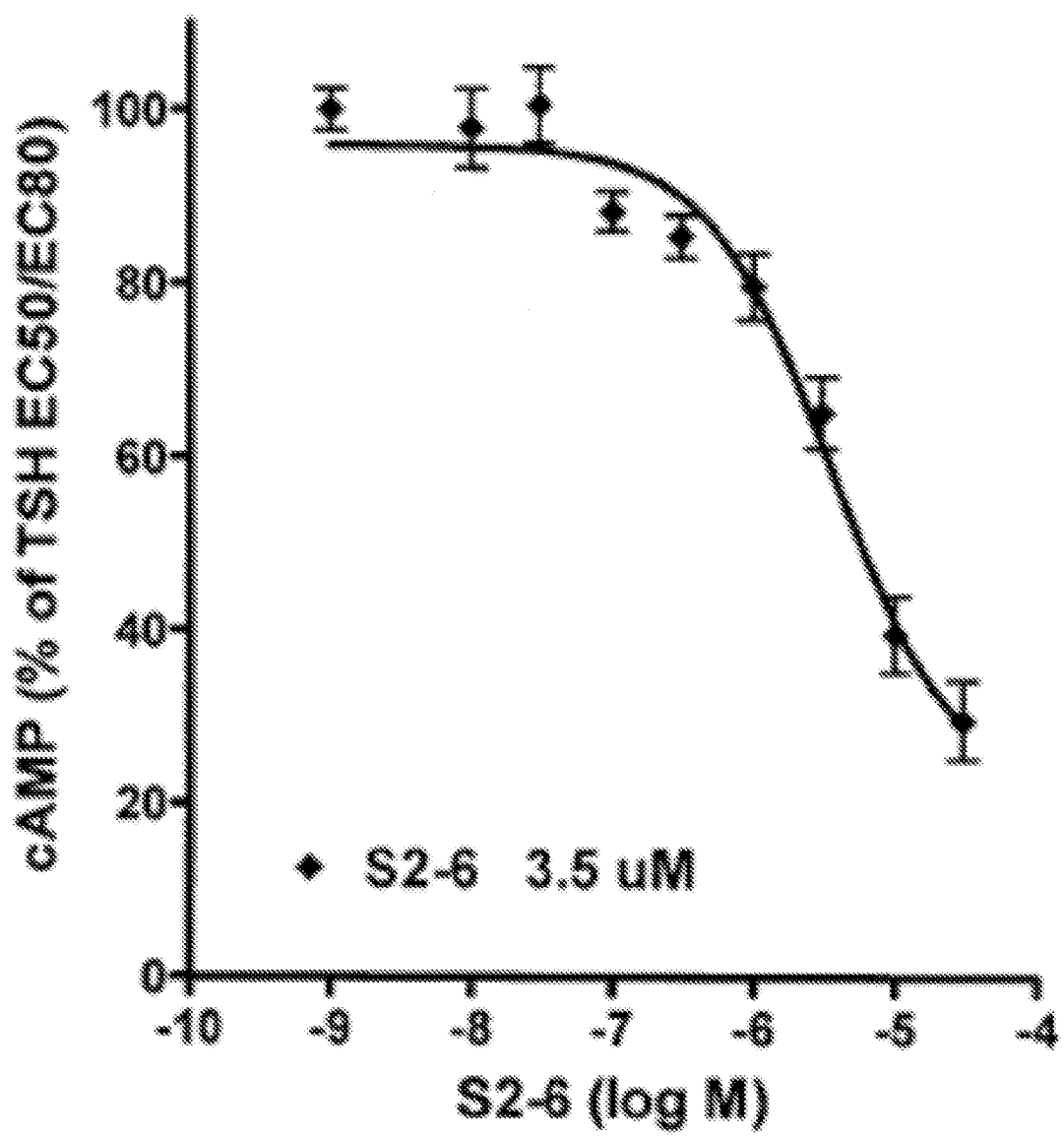
Figure 9:
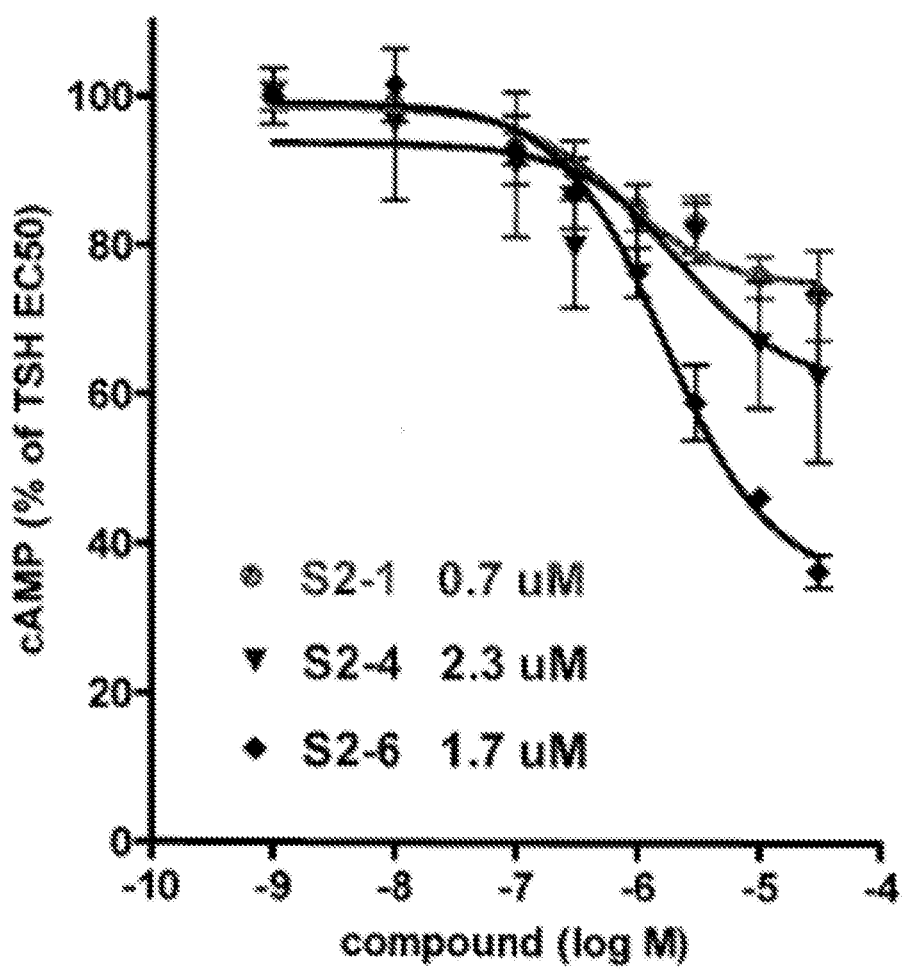

FIGS. 7-9 are dose response curves showing that compound S2-6 is an inverse agonist.

Figure 10:
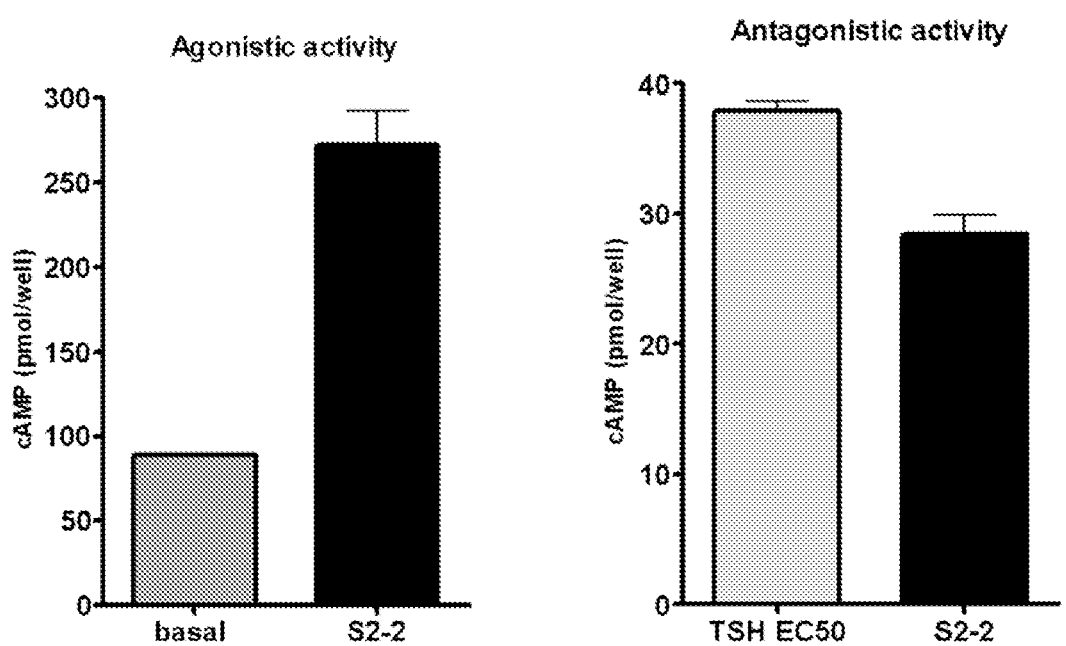

FIG. 10 is a graph showing the TSHR agonistic activity of compound S2-2 and its weak antagonist activity. Agonist activity: HEK-EM 293 cells stably expressing TSHRs were exposed to 30 µM of S2-2 for 60 min in HBSS+1 mM IBMX. Non-treated cells, incubated with IBMX only, were used as control (basal activity). After 60 min, the cells were lysed and cAMP levels were measured by ELISA. Antagonist activity: HEKTSHR cells were exposed to 30 µM of S2-2 for 20 min in HBSS and then were incubated in HBSS with 1 mM IBMX, S2-2 and 1 mU/ml TSH (EC50 dose). After 40 min, the incubation was stopped and total cAMP levels were measured by ELISA.

Figure 11:
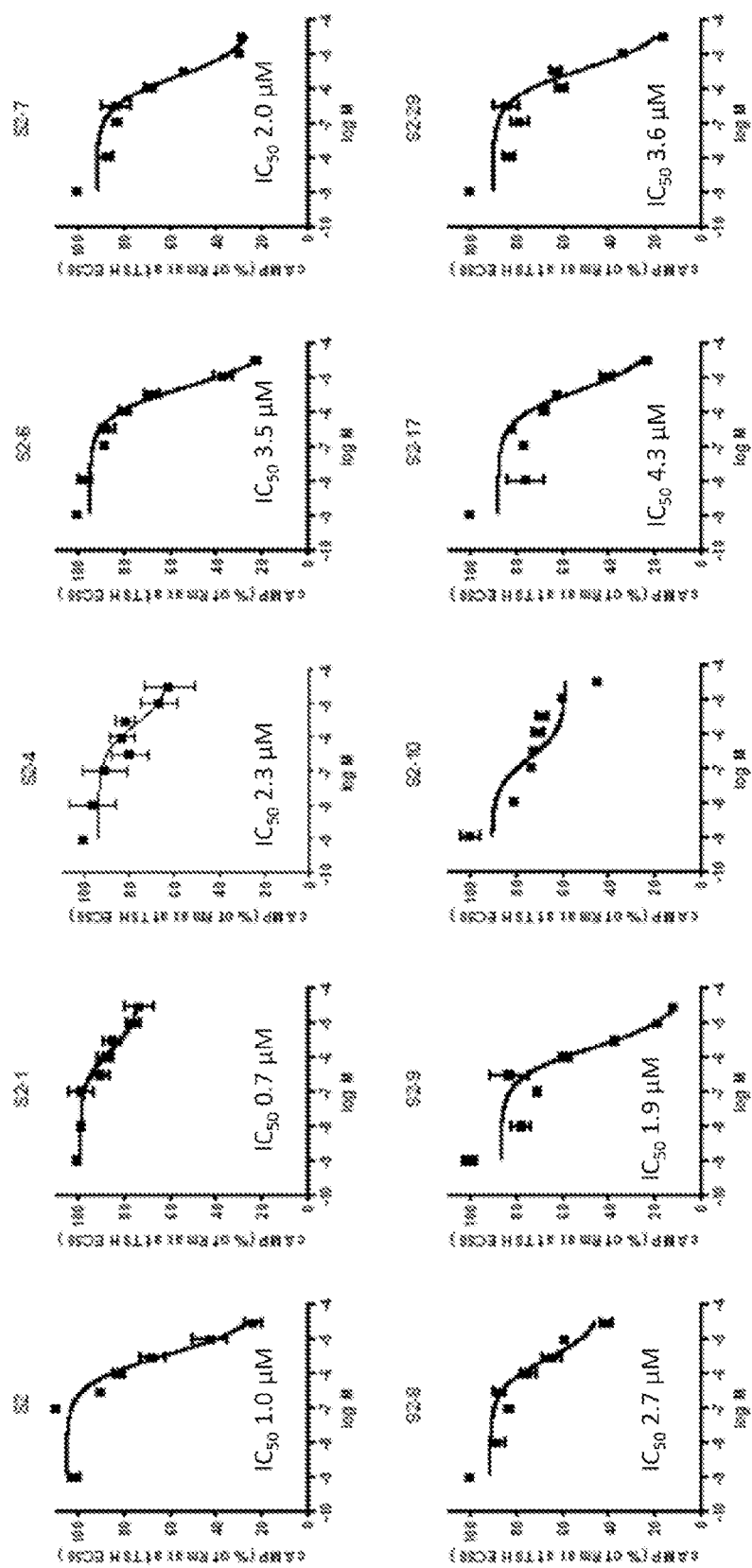

FIG. 11 depicts dose response curves demonstrating that small molecule ligands S2, S2-6, S2-7, S2-8, S2-17 and S2-29 are neutral antagonists. HEKTSHR cells were exposed to the indicated concentrations of the small molecule ligands for 20 min in HBSS and then were incubated in HBSS with 1 mM IBMX, small molecule ligands and 1 mU/ml hTSH (EC50 dose). After 40 min, the incubation was stopped and total cAMP levels were measured by ELISA. The data are from 2 experiments with duplicate samples and are presented as mean±SE.

Figure 12:
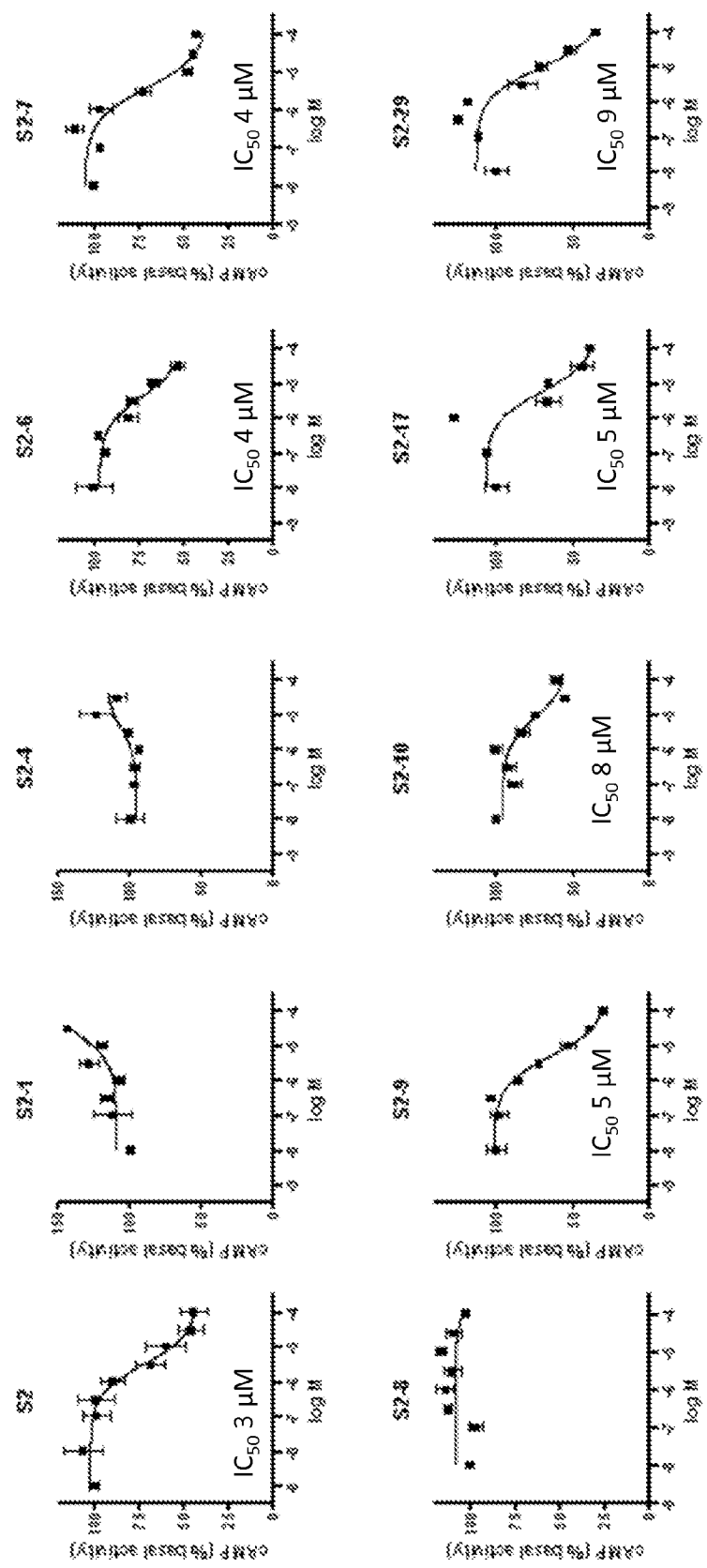

FIG. 12 depicts dose response curves demonstrating that small molecule ligands S2, S2-6 and S2-7 are inverse agonists. All ligands except S2-8 have inverse agonist properties. S2-8 is a neutral antagonist. HEK-EM 293 cells stably expressing TSHRs were exposed to the noted concentrations of the small molecule ligands for 60 min in HBSS+1 mM IBMX. Non-treated cells, incubated with IBMX only, were used as control (basal activity). After 60 min, the cells were lysed and cAMP levels were measured by ELISA. The data from two independent experiments with duplicate samples are shown as % of basal activity.

Figure 13A:
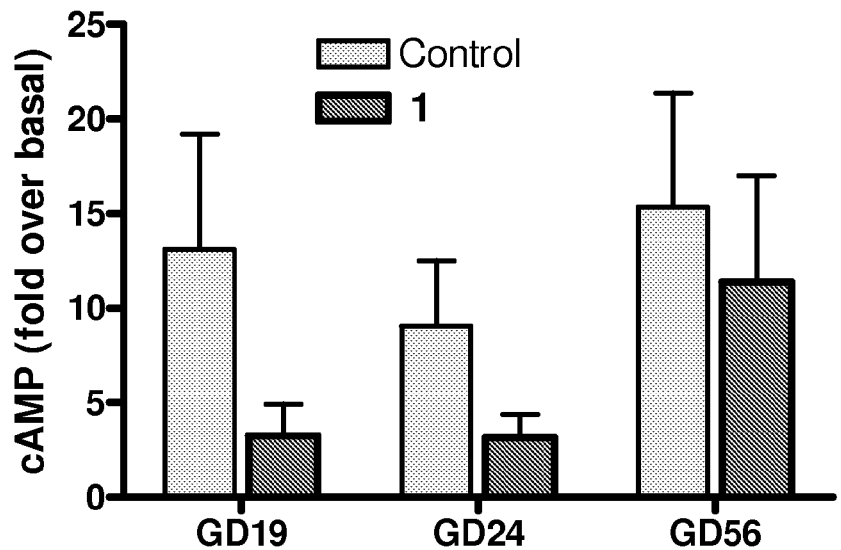
Figure 13B:
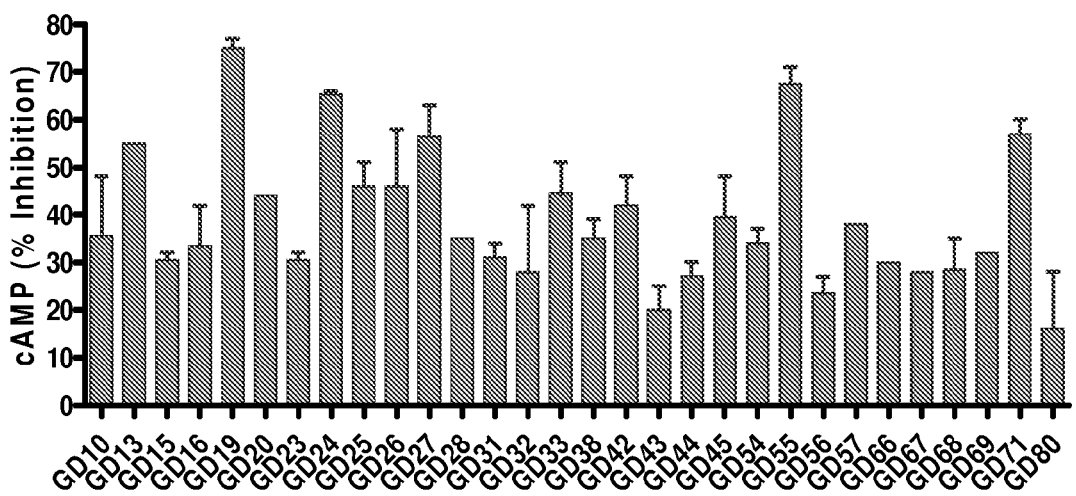

FIGS. 13A and 13B. Compound S2-6 is an antagonist of GD sera stimulation of cAMP production.

FIG. 13A. HEKTSHR cells were incubated without (Control) or with 30 µM Compound S2-6 (designated compound 1 in FIGS. 13A and 13B) for 20 min and then 1 mM IBMX and 1:30 or 1:100 dilutions of each of three GD sera were added. After an additional 40 min, the incubation was stopped and total cAMP levels were measured by ELISA. The data are from one experiment with triplicate samples and are representative of 3 experiments. The effects of compound S2-6 were significant by paired t-test (P<0.01).

FIG. 13B. HEKTSHR cells were incubated without (Control) or with 30 µM compound S2-6 for 20 min and then 1 mM IBMX and 1:30 dilutions of thirty GD sera were added. After an additional 40 min, the incubation was stopped and total cAMP levels were measured by ELISA. The data are presented as % inhibition=100−(100×samples exposed to compound S2-6/Control). The data are representative of 2 experiments performed in duplicate.

Figure 14B:
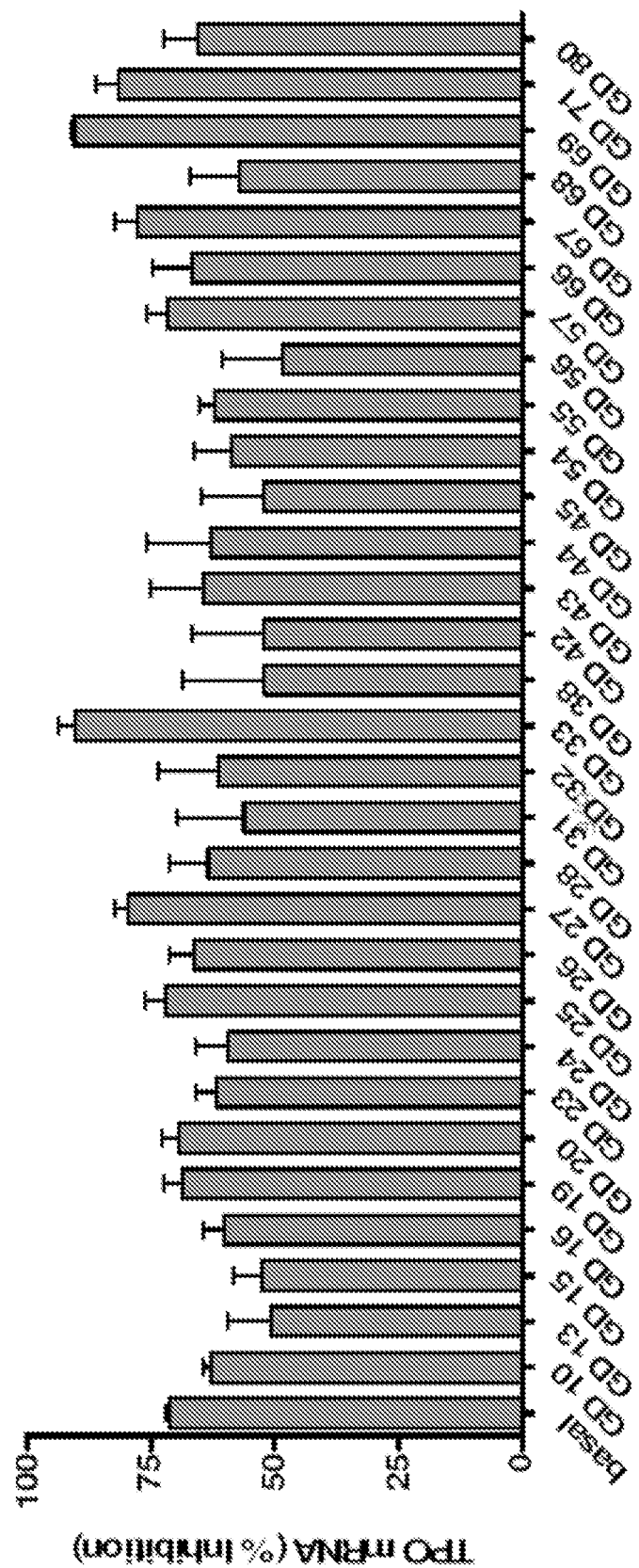

FIGS. 14A and B. Inhibition of basal and TSAb-induced up-regulation of the expression of TPO mRNA by compound S2-6 (designated compound 1 in FIG. 14A) in primary cultures of human thyrocytes. Thyrocytes were incubated in DMEM containing 2% fetal bovine serum without (Control) or with 30 µM compound S2-6 without (basal) or with 1:10 dilutions of GD sera at 37 C. After 48 hr, the buffers were aspirated, the cells were lysed and the levels of TPO mRNA were measured and normalized to GAPDH mRNA. The mRNA levels are presented as fold of basal levels (Control). The data from 2 independent experiments with duplicate samples are shown.

FIG. 15 is a table showing the activity of several compounds.

DETAILED DESCRIPTION

Terminology

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B.

"Administration of" and "administering a" compound should be understood to mean providing a compound, a prodrug of a compound, or a pharmaceutical composition as described herein. The compound or composition can be administered by another person to the subject (e.g., intravenously) or it can be self-administered by the subject (e.g., tablets).

"Optional" or "optionally" means that the subsequently described event or circumstance can but does not need to occur, and that the description includes instances where said event or circumstance occurs and instances where it does not.

"Derivative" refers to a compound or portion of a compound that is derived from or is theoretically derivable from a parent compound.

The term "subject" includes both human and veterinary subjects.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease or condition, for example, in a subject who is at risk for a disease such as a hormone receptor mediated disorder, particularly a thyroid disorder, such as a hyperthyroid or hypothyroid disorder. A "prophylactic" treatment is a treatment administered to a subject who does not exhibit signs of a disease or exhibits only early signs for the purpose of decreasing the risk of developing pathology. By the term "coadminister" is meant that each of at least two compounds be administered during a time frame wherein the respective periods of biological activity overlap. Thus, the term includes sequential as well as coextensive administration of two or more drug compounds.

The term "pharmaceutically acceptable salt or ester" refers to salts or esters prepared by conventional means that include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977). "Pharmaceutically acceptable esters" includes those derived from compounds described herein that are modified to include a hydroxy or a carboxyl group. An in vivo hydrolysable ester is an ester, which is hydrolysed in the human or animal body to produce the parent acid or alcohol. Suitable pharmaceutically acceptable esters for carboxy include $C_{1-6}$ alkoxymethyl esters for example methoxy-methyl, $C_{1-6}$ alkanoyloxymethyl esters for example pivaloyloxymethyl, phthalidyl esters, $C_{3-8}$ cycloalkoxycarbonyloxy$C_{1-6}$ alkyl esters for example 1-cyclohexylcarbonyloxyethyl; 1,3-dioxolen-2-onylmethyl esters for example 5-methyl-1,3-dioxolen-2-onylmethyl; and $C_{1-6}$ alkoxycarbonyloxyethyl esters for example 1-methoxycarbonyl-oxyethyl which may be formed at any carboxy group in the compounds.

An in vivo hydrolysable ester containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxy-methoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

It will be appreciated that the compounds described herein may have metal binding, chelating, complex forming properties and therefore may exist as metal complexes or metal chelates.

"Saturated or unsaturated" includes substituents saturated with hydrogens, substituents completely unsaturated with hydrogens and substituents partially saturated with hydrogens.

The term "acyl" refers group of the formula RC(O)— wherein R is an organic group.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms. Preferred alkyl groups have 1 to 4 carbon atoms. Alkyl groups may be "substituted alkyls"

wherein one or more hydrogen atoms are substituted with a substituent such as halogen, cycloalkyl, alkoxy, amino, hydroxyl, aryl, or carboxyl.

The term "alkenyl" refers to a hydrocarbon group of 2 to 24 carbon atoms and structural formula containing at least one carbon-carbon double bond.

The term "alkynyl" refers to a hydrocarbon group of 2 to 24 carbon atoms and a structural formula containing at least one carbon-carbon triple bond.

The terms "halogenated alkyl" or "haloalkyl group" refer to an alkyl group as defined above with one or more hydrogen atoms present on these groups substituted with a halogen (F, Cl, Br, I).

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous.

The term "aliphatic" is defined as including alkyl, alkenyl, alkynyl, halogenated alkyl and cycloalkyl groups as described above. A "lower aliphatic" group is a branched or unbranched aliphatic group having from 1 to 10 carbon atoms.

The term "alkoxy" refers to a straight, branched or cyclic hydrocarbon configuration and combinations thereof, including from 1 to 20 carbon atoms, preferably from 1 to 8 carbon atoms, more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, or heterocycloalkyl group as described above. Suitable alkoxy groups include methoxy, ethoxy, n-propoxy, i-propoxy, n-butoxy, i-butoxy, sec-butoxy, tert-butoxy cclopropoxy, cyclohexyloxy, and the like.

"Alkoxycarbonyl" refers to an alkoxy substituted carbonyl radical, —C(O)OR, wherein R represents an optionally substituted alkyl, aryl, aralkyl, cycloalkyl, cycloalkylalkyl or similar moiety.

The term "alkyl amino" refers to alkyl groups as defined above where at least one hydrogen atom is replaced with an amino group.

"Aminocarbonyl" alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like. An aminocarbonyl group may be —N(R)—C(O)—R (wherein R is a substituted group or H) or —C(O)—N(R). An "aminocarbonyl" is inclusive of an amido group. A suitable aminocarbonyl group is acetamido.

The term "aryl" refers to any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

"Carbonyl" refers to a radical of the formula —C(O)—. Carbonyl-containing groups include any substituent containing a carbon-oxygen double bond (C=O), including acyl groups, amides, carboxy groups, esters, ureas, carbamates, carbonates and ketones and aldehydes, such as substituents based on —COR or —RCHO where R is an aliphatic, heteroaliphatic, alkyl, heteroalkyl, hydroxyl, or a secondary, tertiary, or quaternary amine.

"Carboxyl" refers to a —COOH radical. Substituted carboxyl refers to —COOR where R is aliphatic, heteroaliphatic, alkyl, heteroalkyl, or a carboxylic acid or ester.

The term "hydroxyl" is represented by the formula —OH.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

The term "amine" or "amino" refers to a group of the formula —NRR', where R and R' can be, independently, hydrogen or an alkyl, alkenyl, alkynyl, aryl, aralkyl, cycloalkyl, halogenated alkyl, or heterocycloalkyl group described above.

The term "amide" or "amido" is represented by the formula —C(O)NRR', where R and R' independently can be a hydrogen, alkyl, alkenyl, alkynyl, aryl, aralkyl, cycloalkyl, halogenated alkyl, or heterocycloalkyl group described above. A suitable amido group is acetamido.

The term "aralkyl" refers to an aryl group having an alkyl group, as defined above, attached to the aryl group, as defined above. An example of an aralkyl group is a benzyl group.

Optionally substituted groups, such as "optionally substituted alkyl," refers to groups, such as an alkyl group, that when substituted, have from 1-5 substituents, typically 1, 2 or 3 substituents, selected from alkoxy, optionally substituted alkoxy, acyl, acylamino, acyloxy, amino, aminoacyl, aminoacyloxy, aryl, carboxyalkyl, optionally substituted cycloalkyl, optionally substituted cycloalkenyl, halogen, optionally substituted heteroaryl, optionally substituted heterocyclyl, hydroxy, sulfonyl, thiol and thioalkoxy. In particular, optionally substituted alkyl groups include, by way of example, haloalkyl groups, such as fluoroalkyl groups, including, without limitation, trifluoromethyl groups.

A "therapeutically effective amount" or "diagnostically effective amount" refers to a quantity of a specified agent sufficient to achieve a desired effect in a subject being treated with that agent. For example, this may be the amount of a compound disclosed herein useful in detecting or treating thyroid cancer in a subject. Ideally, a therapeutically effective amount or diagnostically effective amount of an agent is an amount sufficient to inhibit or treat the disease without causing a substantial cytotoxic effect in the subject. The therapeutically effective amount or diagnostically effective amount of an agent will be dependent on the subject being treated, the severity of the affliction, and the manner of administration of the therapeutic composition.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985).

Pharmaceutically acceptable prodrugs refer to compounds that are metabolized, for example, hydrolyzed or oxidized, in the subject to form an antiviral compound of the present disclosure. Typical examples of prodrugs include compounds that have one or more biologically labile protecting groups on or otherwise blocking a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. In general the prodrug compounds disclosed herein possess hormone receptor modulating activity and/or are metabolized or otherwise processed in vivo to form a compound that exhibits such activity.

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compound also are contemplated. A variety of suitable protecting groups for use with the disclosed compounds are disclosed in Greene and Wuts Protective Groups in Organic Synthesis; 3rd Ed.; John Wiley & Sons, New York, 1999.

In general, protecting groups are removed under conditions which will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS—Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts Protective Groups in Organic Synthesis; 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

It is understood that substituents and substitution patterns of the compounds described herein can be selected by one of ordinary skill in the art to provide compounds that are chemically stable and that can be readily synthesized by techniques known in the art and further by the methods set forth in this disclosure. Reference will now be made in detail to the presently preferred compounds.

Overview

Disclosed herein are compounds that are neutral antagonists of TSHR, that is, they inhibit signaling stimulated by TSH or TSAbs, and inverse agonists that inhibit signaling stimulated by TSH and TSAbs and also inhibit basal signaling.

As mentioned above, activation of TSHR by its endogenous hormone TSH is required for normal thyroid homeostasis but may also regulate the function of thyroid including adipocyte (fat) precursor cells, adipocytes, fibroblasts, immune cells and bone. The TSHR also exhibits activity that does not depend on stimulation by TSH; this is termed agonist-independent, basal or constitutive activity. Agonist-independent signaling activity is thought to be important in some thyroid disease states (see below).

TSHR in thyroid cells, and likely in fibroblasts and adipocytes in the supporting tissue behind the eye (in the retro-orbital space), also are stimulated by TSHR-stimulating antibodies (TSAbs), resulting in Graves' disease. Graves' disease, which is an autoimmune disease that occurs in 1% of the US population, has two important clinical components—1) hyperthyroidism from stimulation of TSHR on thyroid cells and 2) Graves' orbitopathy (or Graves' ophthalmopathy or thyroid eye disease), which appears to result from stimulation of TSHR on retro-orbital fibroblasts and/or adipocytes.

Graves' hyperthyroidism is a hypermetabolic state that affects virtually every tissue/cell in the body and can lead to, in particular, cardiovascular dysfunction and death. Graves' hyperthyroidism can be treated by surgical resection, therapeutic doses of radioactive iodine, or pharmacologically (methimazole or propylthiouracil). However, each of these treatment modalities has side effects associated with it (Cooper D S, 2005 N Engl J Med, 352, 905-917).

Graves' orbitopathy occurs in 80% of Graves' hyperthyroid patients as diagnosed by computerized tomographic scan. Symptoms range from mild to moderate to severe to sight-threatening. Protrusion of the eyeball (proptosis) and varying degrees of extra-ocular muscle weakness or paralysis leading to double vision (diplopia) can be disfiguring and incapacitating. Treatment with glucocorticoids may give some improvement, but correction of the hyperthyroid state to normal has no effect. Vision can be threatened by corneal abrasion or pressure on the optic nerve, requiring emergency therapy using intravenous glucocorticoids and orbital radiotherapy, and in some cases surgical decompression of the orbit (Bahn R S 2010, N Engl J Med 362, 726-738). There is no simple therapy without untoward side effects for Graves' orbitopathy.

The treatment of Graves' hyperthyroidism by surgery, radioactive iodine or drugs that block thyroid hormone synthesis (methimazole or propylthiouracil) reduces or abolishes the hyperthyroid state but does not address the root cause of Graves' hyperthyroidism or Graves' orbitopathy, the presence of TSHR activating antibodies stimulating thyroid or retro-orbital cells and, therefore, does not treat Graves' orbitopathy. Both TSHR inverse agonists and neutral antagonists may be effective therapies for Graves' hyperthyroidism and Graves' orbitopathy since they block stimulation of the TSHR by TSHR-stimulating autoantibodies in thyroid and retro-orbital cells.

A second disease that can be treated by TSHR inverse agonists and neutral antagonists is thyroid cancer. TSHR is expressed in thyroid cancer cells and regulates the growth, proliferation and metastatic potential of thyroid cancer cells. The thyroid gland is, as is well known, one site of metabolic control within the body. Cancer of the thyroid gland is not particularly common, but the high rate of disease re-occurrence necessitates long term surveillance. Usually, during treatment for cancer of the thyroid, the majority of the thyroid tumor is removed, but a small amount often remains that must be treated by radioactive iodide therapy. Indeed, thyroid cancer is characterized by a high likelihood of relapses in up to 30% of patient, even after successful therapy. Therefore, follow-up screening is necessary.

Thyroid hormone suppression of pituitary TSH is usually recommended following primary thyroid cancer treatment (surgical or radioiodine ablation) to lower serum TSH levels and thereby inhibit TSH stimulation of cancer cell growth, proliferation and metastasis. However, administration of thyroid hormone is contraindicated in patients who have cardiovascular problems because of increased risk of arrhythmia and other adverse cardiovascular effects. Inverse agonists and neutral antagonists could suppress tumor growth by inhibiting TSHR activity in patients in whom pituitary TSH cannot be suppressed. In some cases, thyroid cancer recurs despite suppression of TSH by administered thyroid hormones. This may be due to the agonist-independent growth- and proliferation-promoting activity of the constitutively active TSHR. Inverse agonists (which inhibit constitutive TSHR activity) could be effective treatments.

In rare cases, the TSHR contains a hereditary mutation that makes it more active than the normal TSHR, resulting in hereditary non-immune hyperthyroidism. Inverse agonists of the TSHR could be effective treatment for these patients also.

An "inverse agonist" as used herein refers to an agent that inhibits basal or TSH-independent or constitutive TSHR activity. The inverse agonist may also be an antagonist that inhibits TSH activation. In particular, an "inverse agonist" as used herein refers to an agent that inhibits TSH- and thyroid-stimulating antibodies-independent (basal or constitutive) TSHR activity as well as inhibiting TSH- and thyroid-stimulating antibodies-dependent activation. By contrast, a "neutral antagonist" blocks the action of the agonists (TSH or thyroid-stimulating antibodies for TSHR), but does not inhibit basal/constitutive TSHR activity. Thus, inverse agonists and neutral antagonists both antagonize the activation of TSHR by TSH and thyroid-stimulating antibodies. Small-molecule ligands for the TSHR (agonists, inverse agonists, neutral antagonists) bind to an intra-membrane domain of the receptor, and act by inducing a conformational change rather than simply competing for TSH binding to its extracellular site on the receptor.

Small molecule (for example, less than 1000 daltons) inverse agonists and neutral antagonists are attractive agents because they are more easily employed as probes and drugs compared to TSH, its analogs or anti-TSHR antibodies, can be synthesized chemically in large amounts at moderate cost, and can be given orally because they are not degraded within, and can be absorbed from, the gastrointestinal tract. Disclosed herein are inverse agonists that inhibit basal signaling by wild-type TSHR and several constitutively active mutants receptors (CAMs) that may be used for probes of TSHR biology, treating subjects with thyroid cancer (especially TSH-independent thyroid cancer), treating subjects with hyperthyroidism (especially Graves' hyperthyroidism), or treating subjects with Graves' orbitopathy. Also disclosed are neutral antagonists that may be used for probes of TSHR biology or treating subjects with Graves' orbitopathy and/or Graves' hyperthyroidism. In certain embodiments, the inverse agonists and neutral antagonists may be selective inverse agonists or neutral antagonists for TSHR (i.e, the compounds do not activate or modulate other hormone receptors, particularly luteinizing hormone/chorionic gonadotropin receptor (LHCGR) and follicle-stimulating hormone receptor (FSHR)).

In certain embodiments, the inverse agonists disclosed herein may be used for inhibiting cancerous cell growth/proliferation/metastasis in subjects with thyroid cancer despite suppression of their TSH by administered thyroid hormones. Although TSH may be suppressed in subjects treated for thyroid cancer by administering thyroid hormones, TSHRs exhibit basal signaling activity that continues to stimulate thyroid cancer cells. The inverse agonists disclosed herein can inhibit the TSHR basal signaling activity. Thus, in a further embodiment, there is disclosed a method of treating thyroid cancer especially in a subject in whom the cancer recurs despite suppression of his/her endogenous pituitary TSH or when administration of thyroid hormone is contraindicated, comprising administering at least one inverse agonist to the subject.

In certain embodiments, the inverse agonists and neutral antagonists disclosed herein may be used for treating hyperthyroidism in a subject. For example, the inverse agonists and neutral antagonists may inhibit mutant TSHRs with higher than normal basal signaling activities (CAMs) that cause an unusual form of hyperthyroidism. In another example, the inverse agonists and neutral antagonists may inhibit stimulation by antibodies found in Graves' disease, which is the most common form of hyperthyroidism.

In certain embodiments, the inverse agonists are also TSHR antagonists and thus are also useful for treating TSHR-mediated thyroid cancer or hyperthyroidism by blocking TSHR-stimulating antibodies (TSAbs) in Graves' hyperthyroidism.

In particular, the inverse agonists and neutral antagonists of Formula I or II disclosed herein may be used to inhibit stimulation of thyroid or orbital tissues by blocking TSAbs in Graves' hyperthyroidism and/or Graves' orbitopathy.

Inverse Agonists and/or Neutral Antagonists

In one embodiment, the inverse agonists or neutral antagonists are 2,3-dihydroquinazolin-4-one compounds, particularly, 2-substituted, 3-substituted 2,3-dihydroquinazolin-4-one compounds. The substituent at the 2-position may be, for example, a furanyl-containing group, a pyridinyl-containing group, a thienyl-containing group, hydroxyalkyl, or alkoxyalkyl. The substituent at the 3-position may be, for example, —Ar$^1$—CH$_2$—X—Ar$^2$, wherein Ar$^1$ is a substituted or unsubstituted arylene group (e.g., —C$_6$H$_4$—); Ar$^2$ is a substituted or unsubstituted aryl group; and X is O or S. In certain embodiments, Ar$^2$ is 2,6-dialkyl phenyl, particularly 2,6-dimethyl. In certain embodiments, Ar$^1$ is methoxy-substituted phenylene.

In general, illustrative inverse agonists or neutral antagonists may have a structure of:

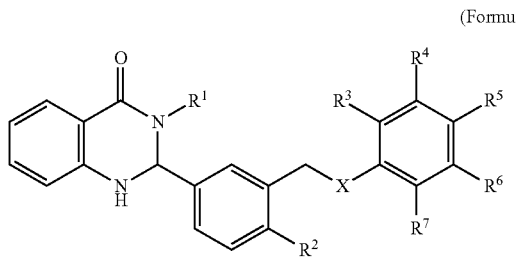
(Formula I)

wherein $R^1$ is selected from a furanyl-containing group, a pyridinyl-containing group, a thienyl-containing group, hydroxyalkyl, or alkoxyalkyl;
$R^2$ is H, alkoxy, alkyl, substituted alkyl or halogen; and
$R^3$-$R^7$ are each individually selected from H, alkyl, substituted alkyl, halogen, or aminocarbonyl; and
X is O or S.

In certain embodiments of Formula I, $R^1$ is selected from:
(a) a furanyl-containing group, wherein the furanyl-containing group is a furanylalkyl group having the structure —$R^{10}$-furanyl, wherein $R^{10}$ is a lower alkylene group (for example, having from 1 to 10 carbon atoms such as methylene (—CH$_2$—), ethylene (—CH$_2$CH$_2$—), trimethylene (—CH$_2$CH$_2$CH$_2$—), methylethylene (—CH$_2$C(CH$_3$)H—), etc.). The furanyl ring may be unsubstituted or substituted with a lower alkyl. In certain embodiments, the furanyl ring is substituted at the 3 carbon position with a lower alkyl, particularly methyl. The furanyl may be 2-furanyl or 3-furanyl. In certain embodiments, the furanyl-containing group is 2-furanyl or furan-2-ylmethyl;
(b) a pyridinyl-containing group, wherein the pyridinyl-containing group is a pyridinylalkyl group having the structure —$R^{10}$-pyridinyl, wherein $R^{10}$ is a lower alkylene group (for example, having from 1 to 10 carbon atoms such as methylene (—CH$_2$—), ethylene (—CH$_2$CH$_2$—), trimethylene (—CH$_2$CH$_2$CH$_2$—), methylethylene (—CH$_2$C(CH$_3$)H—), etc.). The pyridinyl ring may be unsubstituted or substituted with a lower alkyl. The pyridinyl may be 2-pyridinyl, 3-pyridinyl, or 4-pyridinyl. In certain embodiments, the furanyl-containing group is 3-pyridinyl or pyridin-3-ylmethyl;
(c) a thienyl-containing group, wherein the thienyl-containing group is a thienylalkyl group having the structure —$R^{10}$-thienyl, wherein $R^{10}$ is a lower alkylene group (for example, having from 1 to 10 carbon atoms such as methylene (—CH$_2$—), ethylene (—CH$_2$CH$_2$—), trimethylene (—CH$_2$CH$_2$CH$_2$—), methylethylene (—CH$_2$C(CH$_3$) H—), etc.). The thienyl ring may be unsubstituted or substituted with a lower alkyl. In certain embodiments, the thienyl ring is substituted at the 3 carbon position with a lower alkyl, particularly methyl. The thienyl may be 2-thienyl or 3-thienyl. In certain embodiments, the thienyl-containing group is 2-thienyl or thien-2-ylmethyl; or
(d) an alkoxyalkyl having a structure of —$R^8$O$R^9$, wherein $R^8$ is a lower alkylene group (for example, having from 1 to 10 carbon atoms such as methylene (—CH$_2$—), ethylene (—CH$_2$CH$_2$—), trimethylene (—CH$_2$CH$_2$CH$_2$—), methylethylene (—CH$_2$C(CH$_3$)H—), etc.), and $R^9$ is a lower alkyl (particularly methyl); $R^2$ is a lower alkyl group; $R^3$ and $R^7$ are each a lower alkyl group; $R^4$ and $R^6$ are each H; and $R^5$ is an aminocarbonyl group (particularly acetamido (—NHAc or —NHC(O)CH$_3$)) or H.

In particular embodiments of Formula I, $R^3$ and $R^7$ are each a lower alkyl, particularly methyl. In other embodiments of Formula I, $R^2$ is methoxy. In further embodiments of Formula I, —$R^8$O$R^9$ is —(CH$_2$)$_2$OCH$_3$. In additional embodiments of Formula I, X is S. In other embodiments of Formula I, $R^5$ is an aminocarbonyl group. According to another embodiment of Formula I, $R^1$ is —$R^8$O$R^9$. In additional embodiments of Formula I, $R^3$ and $R^7$ are alkyl groups, particularly lower alkyl groups, other than methyl. In further embodiments of Formula I, one of $R^3$ or $R^7$ is a lower alkyl, and the other one of $R^3$ or $R^7$ is H.

In another embodiment, illustrative inverse agonists or neutral antagonists may have a structure of:

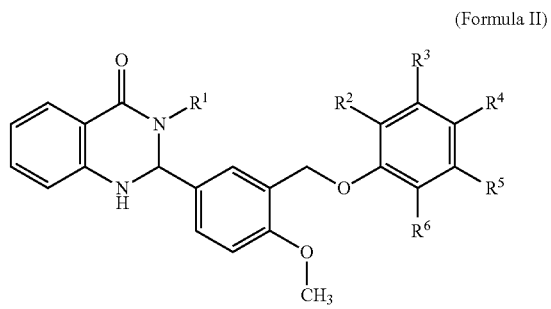
(Formula II)

wherein $R^1$ is selected from:

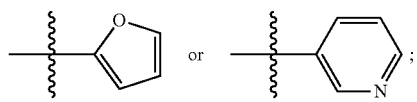 [SMILES: *c1ccco1 ; *c1cccnc1]

and
$R^2$-$R^6$ are each individually selected from H, alkyl, substituted alkyl or halogen; provided that the compound is not

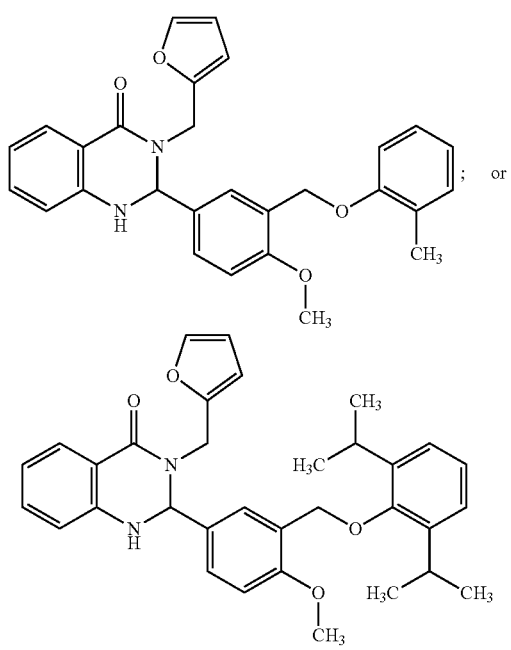

In certain embodiments of Formula II, $R^1$ is:

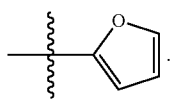

In other embodiments of Formula II, $R^6$ is:

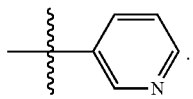 [SMILES: *c1cccnc1]

In certain embodiments of Formula II, $R^2$-$R^6$ are each individually selected from H or alkyl (particularly lower alkyl). In one particular embodiment of Formula II, $R^3$-$R^5$ are each H and $R^2$ and $R^6$ are lower alkyl, especially methyl.

Specific examples of inverse agonists are shown below:

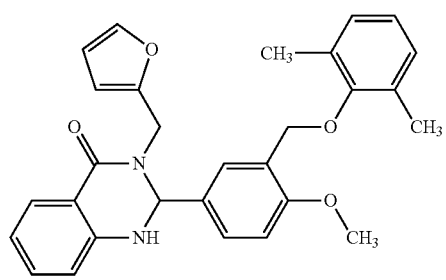 [SMILES: COc1ccc(C2Nc3ccccc3C(=O)N2Cc2ccco2)cc1COc1c(C)cccc1C]

Compound 1 (also referred to herein as compound S2) (NCGC00161856)

Compound S2-6

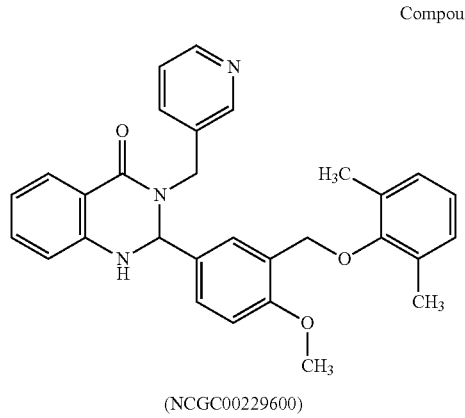

(NCGC00229600)

Compound S2-7

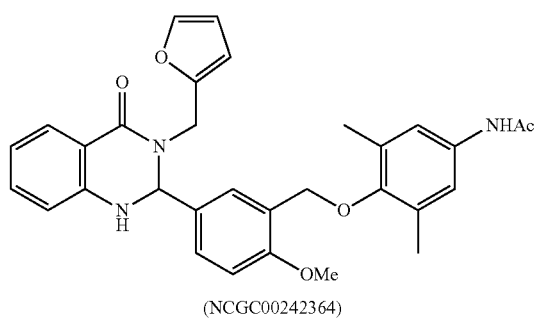

(NCGC00242364)

Specific examples of neutral antagonists are shown below:

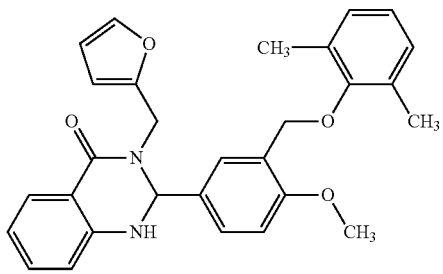 [SMILES: COc1ccc(C2Nc3ccccc3C(=O)N2Cc2ccco2)cc1COc1c(C)cccc1C]

Compound 1 (also referred to herein as compound S2) (NCGC00161856)

Compound S2-6

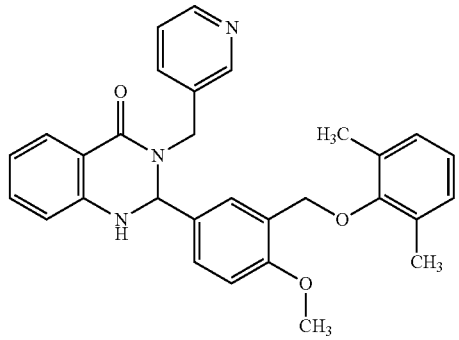

(NCGC00229600)

Compound S2-7

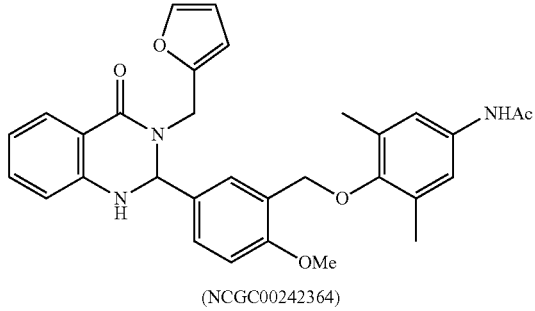

(NCGC00242364)

Compound S2-8

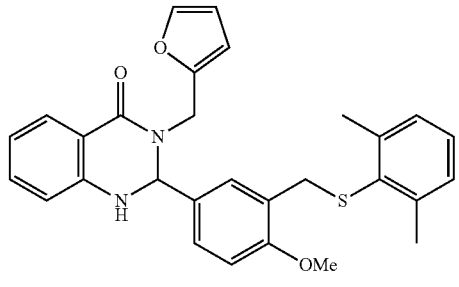

(NCGC00242595)

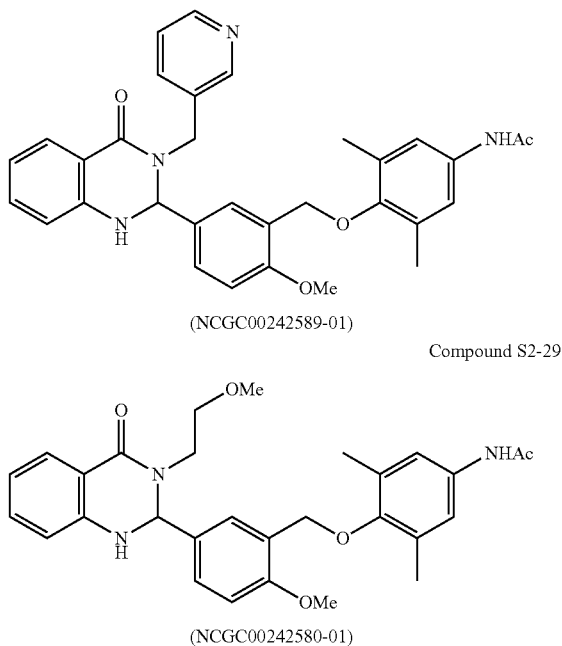

Compound S2-17
(NCGC00242589-01)

Compound S2-29
(NCGC00242580-01)

Pharmaceutical Compositions

Another aspect of the disclosure includes pharmaceutical compositions prepared for administration to a subject and which include a therapeutically effective amount of one or more of the compounds disclosed herein. In certain embodiments, the pharmaceutical compositions are useful for treating thyroid cancer, hyperthyroidism (particularly Graves' hyperthyroidism), or Graves' orbitopathy. The therapeutically effective amount of a disclosed compound will depend on the route of administration, the species of subject and the physical characteristics of the subject being treated. Specific factors that can be taken into account include disease severity and stage, weight, diet and concurrent medications. The relationship of these factors to determining a therapeutically effective amount of the disclosed compounds is understood by those of skill in the art.

Pharmaceutical compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical compositions disclosed herein include those formed from pharmaceutically acceptable salts and/or solvates of the disclosed compounds. Pharmaceutically acceptable salts include those derived from pharmaceutically acceptable inorganic or organic bases and acids. Particular disclosed compounds possess at least one basic group that can form acid-base salts with acids. Examples of basic groups include, but are not limited to, amino and imino groups. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid. In particular, suitable salts include those derived from alkali metals such as potassium and sodium, alkaline earth metals such as calcium and magnesium, among numerous other acids well known in the pharmaceutical art.

Certain compounds include at least one acidic group that can form an acid-base salt with an inorganic or organic base. Examples of salts formed from inorganic bases include salts of the presently disclosed compounds with alkali metals such as potassium and sodium, alkaline earth metals, including calcium and magnesium and the like. Similarly, salts of acidic compounds with an organic base, such as an amine (as used herein terms that refer to amines should be understood to include their conjugate acids unless the context clearly indicates that the free amine is intended) are contemplated, including salts formed with basic amino acids, aliphatic amines, heterocyclic amines, aromatic amines, pyridines, guanidines and amidines. Of the aliphatic amines, the acyclic aliphatic amines, and cyclic and acyclic di- and tri-alkylamines are particularly suitable for use in the disclosed compounds. In addition, quaternary ammonium counterions also can be used.

Particular examples of suitable amine bases (and their corresponding ammonium ions) for use in the present compounds include, without limitation, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl) amine, 2-hydroxy-tert-butylamine, tris(hydroxymethyl)methylamine, N,N-dimethyl-N-(2-hydroxyethyl)amine, tri-(2-hydroxyethyl)amine and N-methyl-D-glucamine. For additional examples of "pharmacologically acceptable salts," see Berge et al., *J. Pharm. Sci.* 66:1 (1977).

Compounds disclosed herein can be crystallized and can be provided in a single crystalline form or as a combination of different crystal polymorphs. As such, the compounds can be provided in one or more physical form, such as different crystal forms, crystalline, liquid crystalline or non-crystalline (amorphous) forms. Such different physical forms of the compounds can be prepared using, for example different solvents or different mixtures of solvents for recrystallization. Alternatively or additionally, different polymorphs can be prepared, for example, by performing recrystallizations at different temperatures and/or by altering cooling rates during recrystallization. The presence of polymorphs can be determined by X-ray crystallography, or in some cases by another spectroscopic technique, such as solid phase NMR spectroscopy, IR spectroscopy, or by differential scanning calorimetry.

The pharmaceutical compositions can be administered to subjects by a variety of mucosal administration modes, including by oral, rectal, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compound can be administered ex vivo by direct exposure to cells, tissues or organs originating from a subject.

To formulate the pharmaceutical compositions, the compound can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The compound can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The compound can be combined with the base or vehicle according to a variety of methods, and release of the compound can be by diffusion, disintegration of the vehicle, or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly(DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly(epsilon-caprolactone), poly(epsilon-aprolactone-CO-lactic acid), poly(epsilon.-aprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, Sustained and *Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

The administration of the compound of the disclosure can be for either prophylactic or therapeutic purpose. When provided prophylactically, the compound is provided in advance of any symptom. The prophylactic administration of the compound serves to prevent or ameliorate any subsequent disease process. When provided therapeutically, the compound is provided at (or shortly after) the onset of a symptom of disease or infection.

For prophylactic and therapeutic purposes, the compound can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to alleviate one or more symptoms of a targeted disease). In alternative embodiments, an effective amount or effective dose of the compound may simply inhibit or enhance one or more selected biological activities correlated with a disease or condition, as set forth herein, for either therapeutic or diagnostic purposes.

The actual dosage of the compound will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is about 0.01 mg/kg body weight to about 20 mg/kg body weight, such as about 0.05 mg/kg to about 5 mg/kg body weight, or about 0.2 mg/kg to about 2 mg/kg body weight.

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth.

The compounds disclosed herein may also be co-administered with an additional therapeutic agent. Such agents include, but are not limited to, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

The instant disclosure also includes kits, packages and multi-container units containing the herein described pharmaceutical compositions, active ingredients, and/or means for administering the same for use in the prevention and treatment of diseases and other conditions in mammalian subjects. Kits for diagnostic use are also provided. In one embodiment, these kits include a container or formulation that contains one or more of the compounds described herein. In one example, this component is formulated in a pharmaceutical preparation for delivery to a subject. The compound is optionally contained in a bulk dispensing container or unit or multi-unit dosage form. Optional dispensing means can be provided, for example a pulmonary or intranasal spray applicator. Packaging materials optionally include a label or instruction indicating for what treatment purposes and/or in what manner the pharmaceutical agent packaged therewith can be used.

EXAMPLES

Figure 1A:
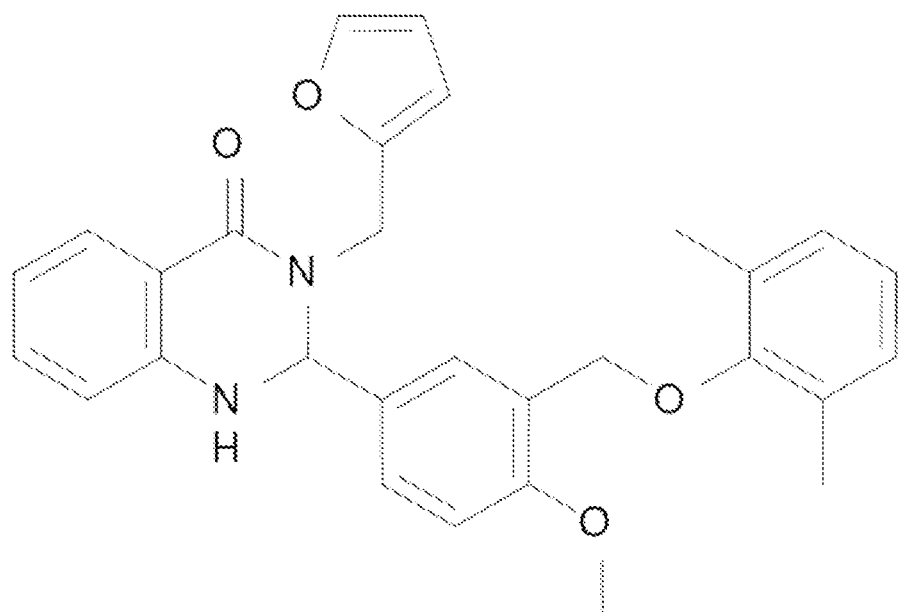
FIGS. 1A and 1B. Structure and effect of compound 1 on agonist-independent signaling by TSHR.
Figure 1B:
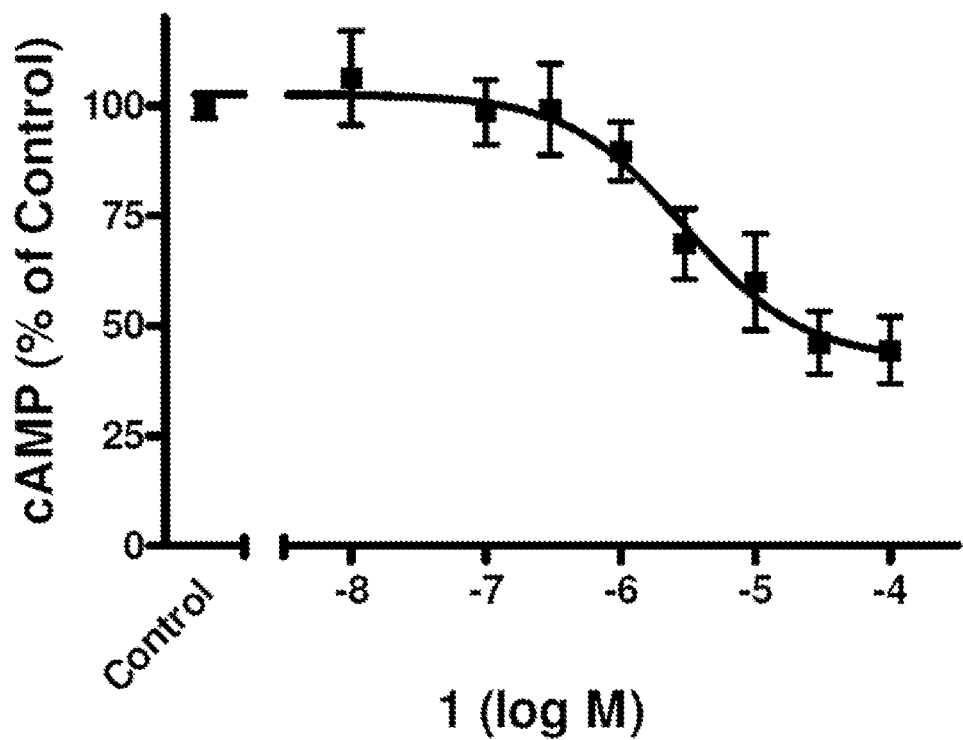
Figure 2A:
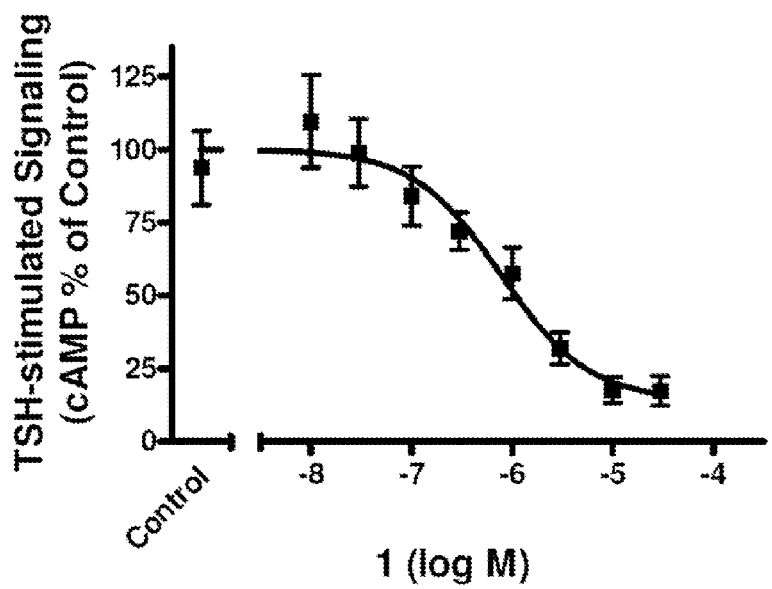
FIGS. 2A and 2B. Compound 1 is a competitive antagonist of TSH-stimulated signaling.
Figure 2B:
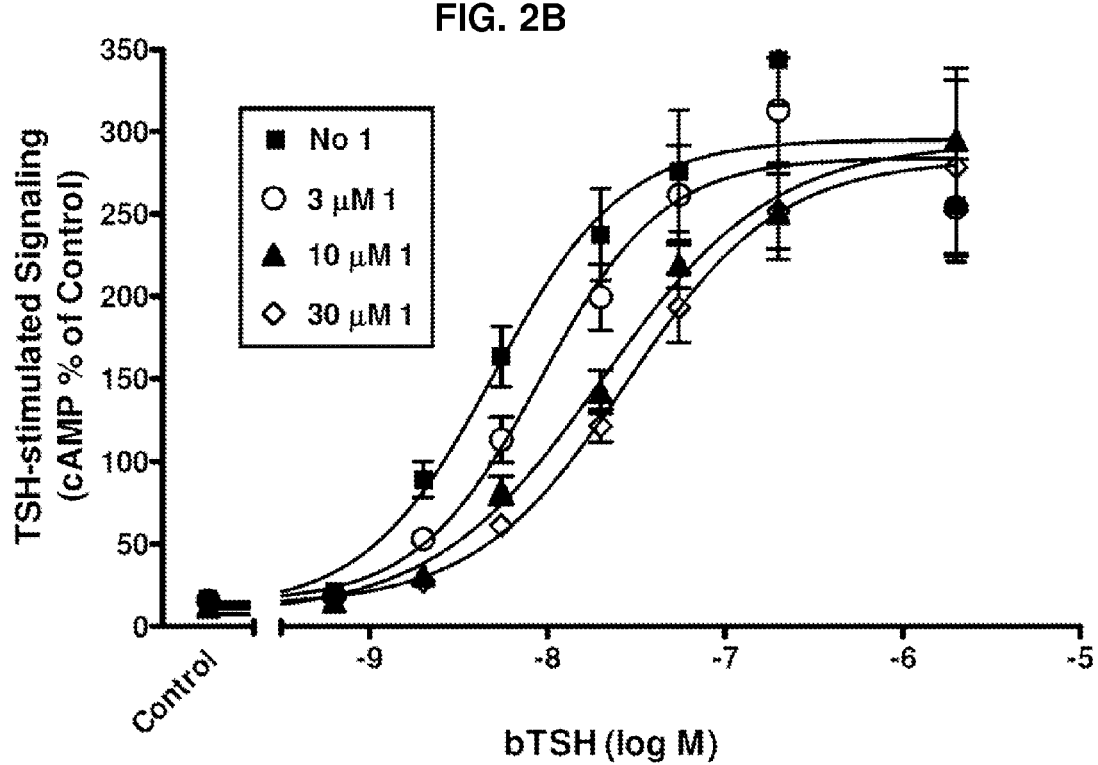

Compound 1 (2-(3-((2,6-dimethylphenoxy)methyl)-4-methoxyphenyl)-3-(furan-2-ylmethyl)-2,3-dihydroquinazolin-4(1H)-one) [NCGC00161856] (FIG. 1A) was found to be an inverse agonist (see FIG. 1B). Compound 1 inhibited basal cAMP production by TSHRs by 58% with an $IC_{50}$=3.0 μM. FIG. 2A illustrates that 1 inhibits TSH-stimulated cAMP production by 86%; $IC_{50}$=0.78 μM. Moreover, a Schild analysis of TSH-stimulated cAMP (FIG. 2B) production shows that 1 acts as a competitive antagonist of TSH signaling (not shown). Competitive antagonism is often caused by binding competition between the antagonist and agonist. However, 1 had no effect on $^{125}$I-TSH binding to TSHRs on the surface of HEK-EM 293 cells (data not shown). A lack of effect of 1 on TSH binding was expected as it has been previously shown that the parent compound of 1 does not affect TSH binding and provided evidence that it binds in the transmembrane domain of TSHR. It is assumed that 1 binds in the same domain of TSHR.

A small number of patients with hyperthyroidism exhibit increased thyroid function caused by basal signaling of constitutively active mutant TSHRs (CAMs). Basal activities, cAMP production over 60 min in HEK-EM 293 cells transiently expressing TSHRs, of wild-type TSHR and four CAMs—S281N, M453T, I568T and F631I were measured—that were found in hyperthyroid patients. These CAMs exhibit constitutive signaling between 15- and 27-fold higher than wild-type TSHR. FIG. 3 illustrates that compound 1 inhibited basal signaling of all 4 CAMs tested with the following $IC_{50}$s and maximum levels of inhibition: 1.4 μM and 78% with S281N, 3.7 μM and 77% with I568T; 0.5 μM and 36% with F631I; and 0.6 μM and 42% with M453T. The levels of inhibition of basal signaling by compound 1 appear to segregate these CAMs into 2 groups with greater inhibition in one than in the other.

The antagonist and inverse agonist activities of compound 1 were measured in human thyrocytes in primary culture, which is a more physiologically relevant cell system that allows for the determination of the effects of TSHR ligands on expression of genes important in differentiated thyroid function. This was important because it has been shown that TSHR mutants signal differently in different cell types. It was first confirmed that compound 1 decreases cAMP accumulation in human thyrocytes (FIG. 4A). Since 1 did not decrease cAMP accumulation stimulated by isoproterenol, an agonist for the 7TMR beta-adrenergic receptor, vasoactive intestinal peptide, which signals via a 7TMR, or forskolin, an adenylyl cyclase activator, in these cells (not shown), we conclude that compound 1 acts as a TSHR inverse agonist in human thyrocytes. TSH and the small molecule ligand agonist that were identified previously specifically increase expression of several genes in thyrocytes (J Biomol Screen 13, 120, 2008; Proc Nat Acad Sci 106, 12471, 2009). The effects of compound 1 on the expression of the mRNAs for these genes—TPO, TSHR, TG and DIO2 were tested—in the absence of any agonist (FIG. 4B). Thyrocytes were treated without or with compound 1 alone in the presence of IBMX for 48 hr. Compound 1 decreased TG, TPO, TSHR, NIS and DIO2 mRNA levels. Thus, compound 1 is an inverse agonist in human thyrocytes that can decrease the levels of mRNAs for several genes expressed in differentiated thyrocytes most likely by inhibiting their transcription. These observations support the idea that compound 1, or an analog thereof, could be used to suppress TSH-independent signaling in humans.

A novel analog of compound 1, S2-6 [2-(3-((2,6-dimethylphenoxy)methyl)-4-methoxyphenyl)-3-(pyridin-3-ylmethyl)-2,3-dihydroquinazolin-4-one] (NCGC00229600) was as potent and effective as compound 1 (NCGC00161856) as a TSHR antagonist but was a better drug because of its increased solubility (J. Clin. Endocrinol. Metab. 96, 548, 2011). We showed that S2-6 is an antagonist of basal and TSH stimulation of TSHR in human cells (see FIGS. 6-9). S2-6 inhibited basal cAMP production by TSHRs by 53% at 30 μM and inhibited cAMP production stimulated by an $EC_{50}$ concentration of TSH by 53% at 30 μM. S2-6 inhibition of cAMP production by was overcome at high doses of TSH and was, therefore, "competitive". Competitive inhibition may have been caused by competition by S2-6 of TSH binding, however, S2-6 had no effect on $^{125}$I-TSH binding to HEKTSHR cells and is, therefore, an allosteric inverse agonist. Most importantly, S2-6 was tested against serums from thirty patients with Graves' hyperthyroidism including at least one patient with Graves' orbitopathy (FIG. 13). S2-6 inhibited cAMP production by 39±2.6% by all thirty Graves' disease sera tested. In primary cultures of human thyrocytes, S2-6 inhibited TSHR-mediated basal and thyroid-stimulating antibodies in Graves' disease sera up-regulation of thyroperoxidase mRNA levels by 65±2.0% (FIG. 14). Thus, S2-6, a small molecule allosteric inverse agonist of TSHR, is a general antagonist of TSH receptor activation by thyroid-stimulating antibodies in Graves' disease patient sera.

There are at least two patient groups in which inverse agonists could be used therapeutically. Patients with non-autoimmune hyperthyroidism caused by constitutively active mutants (CAMs), especially germline mutations, are one group in whom inverse agonists could be effective as it has already been shown that compound 1 and thyroid inhibiting antibodies inhibit basal signaling by disease-associated CAMs expressed in cells in tissue culture. The use of small molecule ligand inverse agonists would perhaps be most valuable in children with inherited forms of this disease in which radioiodine or surgical ablation is less attractive. A larger patient group in which these drugs would be useful are patients with recurrent or metastatic thyroid cancer who are receiving thyroid hormones for TSH suppression but who may still have their cancer cells stimulated to proliferate and metastasize because of the agonist-independent signaling of TSHR.

In a preliminary experiment, it has been shown that compound S2-6 inhibits activation of TSHRs on retro-orbital fibroblasts acquired from patients with Graves' orbitopathy. Retro-orbital fibroblasts were obtained from patients undergoing decompression eye surgery for Graves' orbitopathy and were adapted to cell culture. S2-6 was shown to inhibit basal signaling by 75% and thyroid-stimulating antibody-stimulated signaling (by 85%) in these fibroblasts in cell culture.

The results above show that inverse agonists and neutral antagonists have application, in one illustrative embodiment, as a therapy (e.g, as an initial therapy) for Graves' orbitopathy (which results from stimulating TSHR antibodies acting on retro-orbital TSHRs), and, in another illustrative embodiment, as a therapeutic alternative to surgery for Graves' hyperthyroidism, for example, recurrent Graves' hyperthyroidism (following radioiodine or anti-thyroid drug treatment). Inverse agonists would be useful for patients with recurrent or metastatic thyroid cancer who are receiving thyroid hormones for TSH suppression but who may still have their cancer cells stimulated to proliferate and metastasize because of TSH agonist-independent signaling of TSHR.

Materials and Methods

General Synthesis

All commercially available reagents and solvents were purchased and used without further purification. All microwave reactions were carried out in a sealed microwave vial equipped with a magnetic stir bar and heated in a Biotage Initiator Microwave Synthesizer. $^1$H spectra were recorded using either an Inova 400 MHz spectrometer (Varian). LCMS was used to analyze samples' purity: Agilent 1200 series LC/MS equipped with a Zorbax™ Eclipse XDB-C18 reverse phase (5 micron, 4.6×150 mm) column having a flow rate of 1.1 mL/min. The mobile phase was a mixture of acetonitrile and $H_2O$ each containing 0.05% trifluoroacetic acid. A gradient of 5% to 100% acetonitrile over 8 minutes was used during analytical analysis. High-resolution mass spectroscopy measurements were performed on an Agilent 6210 Electrospray TOF mass spectrometer.

The following general procedures were used to synthesize compounds having different but analogous structures. One skilled in the art of synthesis will recognize how to modify these general procedures if necessary to accomplish the desired transformations.

Scheme 1. Synthesis of dihydroquinazolin-4-one 7

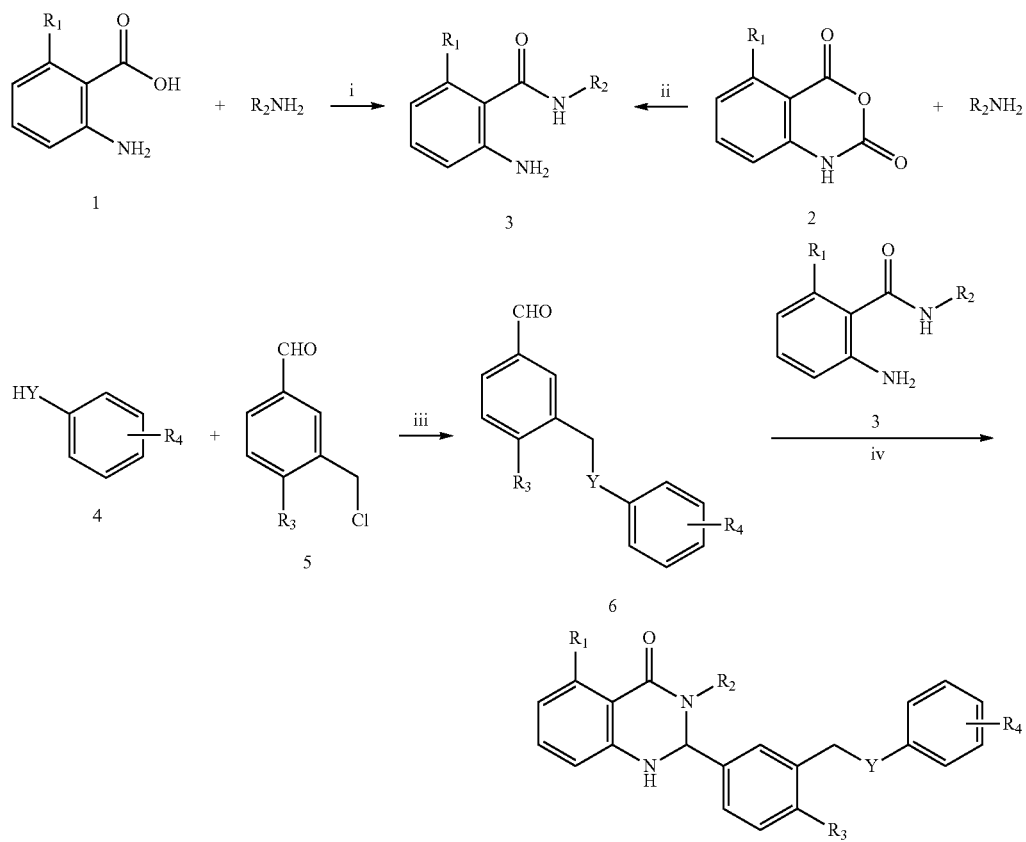

Reagents and conditions: (i) DMC, DIPEA, r.t. 12 h; (ii) ACN, r.t. -50° C. (iii) K$_2$CO$_3$, DMA, microwave heating, 150° C., 10 min; (iv) Yb(OTf)$_3$, EtOH, 80° C., 2-4 h;

As depicted in scheme 1,2-aminobenzamides 3 were prepared by either amide couplings of 2-aminobenzoic acids 1 with different amines or reactions of isatoic anhydrides 2 with amines. Reactions of benzyl chlorides 5 with different phenols (or thiophenols) 4 under microwave irradiation generated aldehydes 6. Condensations of aldehydes 6 with 2-aminobenzamides 3 yielded 2,3-dihydroquinazolin-4-ones 7.

General procedure for the synthesis of 2-aminobenzamides (3) from isatoic anhydride:

Amines (1.05 mmol, 1.05 equiv) at room temperature were added to a solution of isatoic anhydride (0.16 g, 1.0 mmol, 1.0 equiv) in 10 mL of anhydrous acetonitrile. The resulting mixture was stirred at room temperature for 2 h and heated at 50° C. for 4 h. Then, it was concentrated in vacuo to yield the products as solids in 90-99% yields.

2-Amino-N-(furan-2-ylmethyl)benzamide

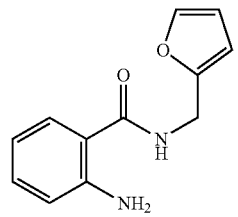 [SMILES: Nc1ccccc1C(=O)NCc1ccco1]

$^1$H NMR (400 MHz, CHLOROFORM-d) δ 4.60 (s, 1 H), 4.61 (s, 1 H), 5.57 (br. s., 2 H), 6.24-6.42 (m, 3 H), 6.59-6.74 (m, 2 H), 7.16-7.25 (m, 1 H), 7.33-7.39 (m, 2 H); LCMS: (electrospray+ve), m/z 217.1 (MH)$^+$; HPLC: $t_R$=3.77 min, UV$_{254}$=98%.

2-Amino-N-(2-methoxyethyl)benzamide

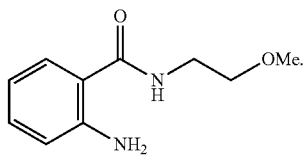

$^1$H NMR (400 MHz, DMSO-d$_6$) δ ppm 3.23 (s, 3 H), 3.28-3.49 (m, 4 H), 6.36 (br. s., 2 H), 6.47 (t, J=7.4 Hz, 1 H), 6.65 (d, J=7.4 Hz, 1 H), 7.00-7.18 (m, 1 H), 7.44 (d, J=6.7 Hz, 1 H), 7.99-8.31 (m, 1 H); LCMS: (electrospray+ve), m/z 195.1 (MH)$^+$; HPLC: $t_R$=2.70 min, UV$_{254}$=95%.

2-Amino-N-(pyridin-3-ylmethyl)benzamide

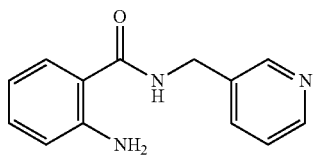 [SMILES: Nc1ccccc1C(=O)NCc1cccnc1]

$^1$H NMR (400 MHz, DMSO-d$_6$) δ ppm 4.41 (d, J=5.9 Hz, 2 H), 6.40 (br. s., 2 H), 6.49 (t, J=7.4 Hz, 1 H), 6.67 (d, J=7.4 Hz, 1 H), 7.12 (t, J=7.0 Hz, 1 H), 7.32 (dd, J=7.6, 4.9 Hz, 1 H), 7.51 (d, J=7.0 Hz, 1 H), 7.68 (d, J=7.8 Hz, 1 H), 8.28-8.69 (m, 2 H), 8.79 (t, J=5.7 Hz, 1 H); LCMS: (electrospray+ve), m/z 228.1 (MH)$^+$; HPLC: $t_R$=2.21 min, UV$_{254}$=95%.

Synthesis of 1 [2-(3-((2,6-dimethylphenoxy)methyl)-4-methoxyphenyl)-3-(furan-2-ylmethyl)-2,3-dihydroquinazolin-4(1H)-one (NCGC00161856)]

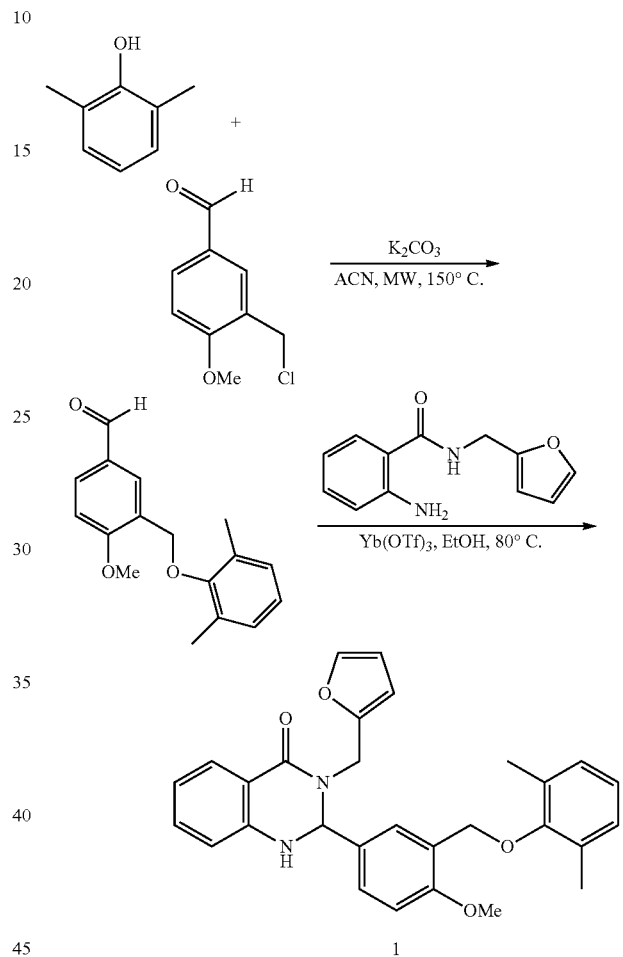

To a solution of 3-(chloromethyl)-4-methoxybenzaldehyde (85 mg, 0.46 mmol, 1.0 equiv) and 2,6-dimethylphenol (62 mg, 0.51 mmol, 1.1 equiv) in 3.0 mL of anhydrous acetonitrile, we added K$_2$CO$_3$ (320 mg, 2.3 mmol, 5.0 eq). The mixture was heated in a microwave reactor for 30 min at 150° C. After filtering off the solid and removing the solvent, 2-amino-N-(furan-2-ylmethyl)benzamide (110 mg, 0.51 umol, 1.1 equiv) in 5 mL of EtOH was added followed by addition of Ytterbium trifluoromethanesulfonate (57 mg, 0.02 umol, 0.2 equiv). The mixture was heated at 80° C. for 2 hours. The product was isolated via preparative HPLC purification and solvent was removed via reduced pressure lyophilization to give 2434(2,6-dimethylphenoxy)methyl)-4-methoxyphenyl)-3-(furan-2-ylmethyl)-2,3-dihydroquinazolin-4(1H)-one (64.5 mg, 30%) as a white solid after triturating with diethyl ether. $^1$HNMR (400 MHz, DMSO-d$_6$) δ ppm 2.16 (s, 6H), 3.77 (s, 3 H), 3.86 (d, J=15.6 Hz, 1 H), 4.69 (d, J=1.9 Hz, 2 H), 5.19 (d, J=15.4 Hz, 1 H), 5.75 (d, J=2.3, Hz, 1 H), 6.30 (d, J=3.2 Hz, 1 H), 6.39 (dd, J=3.2, 1.9 Hz, 1 H), 6.62-6.70 (m, 2 H), 6.86-6.97 (m, 1 H), 6.99-7.04 (m, 3 H), 7.19-7.29 (m, 2 H), 7.32 (d, J=2.3 Hz, 1 H), 7.49 (d, J=2.4, Hz, 1 H), 7.57 (dd, J=1.8, 0.7 Hz, 1 H), 7.68 (dd, J=7.9, 1.5 Hz, 1 H); HPLC: $t_R$=6.88 min, $UV_{254}$=97%; HRMS (ESI): m/z calculated for $C_{29}H_{28}N_2O_4$ $[M+1]^+$ 469.2132, found 469.2138.

Synthesis of S2-6

To a solution of 3-(chloromethyl)-4-methoxybenzaldehyde (300 mg, 1.625 mmol, 1.0 equivalent) and 2,6-dimethylphenol (218 mg, 1.787 mmol, 1.1 equivalent) in 10 ml acetonitrile was added potassium carbonate (1.1 g, 8.12 mmol, 5.0 equivalents). The mixture was heated to 150 C in a microwave for 30 min. Upon completion, the mixture was filtered and dried down to give 3-[(2,6-dimethylphenoxy)methyl]-4-methoxybenzaldehyde (400 mg, 91% yield) as a yellow solid. A portion of which (100 mg, 0.370 mmol, 1.0 equivalent) was taken up in ethanol (4 ml), and to it was added 2-amino-N-(pyridin-3-ylmethyl)benzamide (92 mg, 0.407 mmol, 1.1 equivalent) followed by ytterbium(III) trifluoromethanesulfonate (45.9 mg, 0.074 mmol, 0.2 equivalent). The mixture was heated to 80 C for 2 h. Upon completion, the mixture was dried down and chromatographed on silica gel with 0-30% EtOAc (ethyl acetate)/hexanes gradient elution to give the desired 2-{3-[(2,6-dimethylphenoxy)methyl]-4-methoxyphenyl}-3-(pyridin-3-ylmethyl)-2,3-dihydroquinazolin-4(1H)-one (110 mg, 62.0% yield) as a tan solid. 1H nuclear magnetic resonance (400 MHz, DMSO-$d_6$) δ ppm 8.39-8.45 (m, 2 H), 7.60-7.67 (m, 2 H), 7.48 (d, J=2.35 Hz, 1 H), 7.15-7.35 (m, 4 H), 6.94-7.02 (m, 3 H), 6.84-6.93 (m, 1 H), 6.60-6.69 (m, 2 H), 5.82 (d, J=2.35 Hz, 1 H), 5.07 (d, J=15.65 Hz, 1 H), 4.64 (d, J=2.74 Hz, 2 H), 3.99 (d, J=15.45 Hz, 1 H), 3.73 (s, 3 H), 2.12 (s, 6 H); liquid chromatography mass spectrometry: (electrospray+ve), m/z 480.2 $(MH)^+$ (mass of molecular weight plus 1); HPLC: $t_R$=5.05 min, $UV_{254}$=100%. High-resolution mass spectroscopy (electrospray ionization): m/z calculated for $C_{30}H_{30}N_3O_3$ $[M+H]^+$ 480.2282, found 480.2291.

Synthesis of N-(4-(5-(3-(Furan-2-ylmethyl)-4-oxo-1,2,3,4-tetrahydroquinazolin-2-yl)-2-methoxybenzyloxy)-3,5-dimethylphenyl)acetamide (7a; compound S2-7)

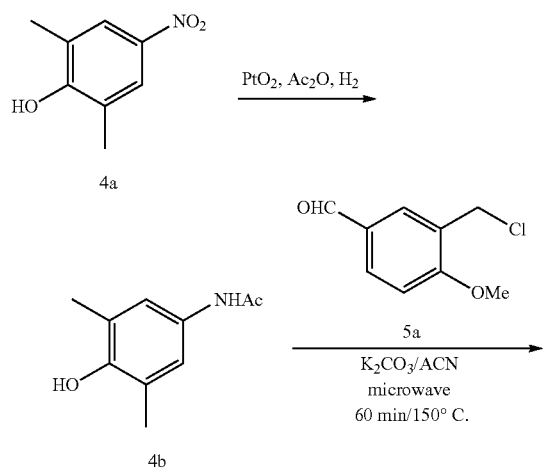

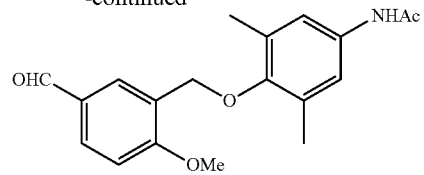

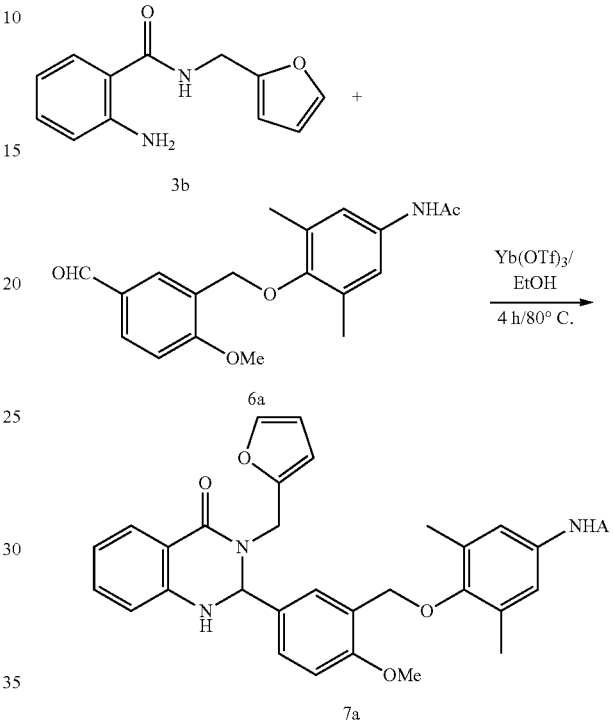

A suspension of 2,6-dimethyl-4-nitrophenol (4a, 1.58 g, 9.45 mmol) in AcOH (20 ml), MeOH (15 ml), and THF (10 ml) in a hydrogenator vessel was treated with acetic anhydride (6 ml, 63.6 mmol) and $PtO_2$ (200 mg, 0.881 mmol), pressurized to 50 p.s.i. with $H_2$ and shaken for 24 h. The reaction mixture was returned to atmospheric pressure, diluted with EtOAc, washed with $H_2O$, dried ($MgSO_4$), filtered and concentrated under reduced pressure. N-(4-hydroxy-3,5-dimethylphenyl)acetamide (4b) was isolated as a white solid that was pure based upon LCMS analysis and used without further purification. Potassium carbonate (810 mg, 5.34 mmol) was added to a solution of tetrabutylammonium iodide (78.9 mg, 0.534 mmol), 3-(chloromethyl)-4-methoxybenzaldehyde (5a, 197 mg, 1.07 mmol), and N-(4-hydroxy-3,5-dimethylphenyl)acetamide (4b, 211 mg, 1.18 mmol) in 20 ml of acetonitrile. The reaction mixture was heated to 150° C. in the microwave for 1 h, filtered and concentrated under reduced pressure. The residue was purified by column chromatography on silica gel with 5-50% EtOAc/DCM gradient to afford the desired product 6a (196 mg, 56%) as a white solid. $^1$H NMR (400 MHz, CHLOROFORM-d) δ ppm 2.15 (s, 3 H), 2.28 (s, 6 H), 3.93 (s, 3 H), 4.83 (s, 2 H), 7.02 (d, J=8.4 Hz, 1H), 7.13 (s, 1 H), 7.17 (s, 2 H), 7.89 (dd, J=8.4, 2.0 Hz, 1 H), 8.12 (d, J=1.8 Hz, 1H), 9.94 (s, 1 H); LCMS: (electrospray+ve), m/z 328.2 $(MH)^+$, $t_R$=3.16 min, $UV_{254}$=>95%. N-(4-(5-formyl-2-methoxybenzyloxy)-3,5-dimethylphenyl) acetamide (6a, 145 mg, 0.441 mmol), 2-amino-N-(furan-2-ylmethyl)benzamide (3b, 105 mg, 0.486 mmol), and 0.2 equiv of $Yb(OTf)_3$ in 5 ml of EtOH were heated at 80° C. for 4 h. The reaction mixture was concentrated under reduced pressure and the residue was chromatographed on silica-gel using 7-60% ethyl acetate in hexanes to give the desired product 7a (40.9 mg, 0.078 mmol, 17.6% yield) as a white solid. $^1$H NMR (400 MHz, CHLOROFORM-d) δ ppm 2.15 (s, 3 H), 2.21 (s, 6 H), 3.77 (d, J=15.7 Hz, 1 H), 3.84 (s, 3 H), 4.41 (s, 1 H), 4.70-4.87 (m, 2 H), 5.35 (d, J=15.7 Hz, 1 H), 5.78 (s, 1 H), 6.20 (d, J=2.9 Hz, 1 H), 6.24-6.32 (m, 1 H), 6.53 (d, J=8.0 Hz, 1 H), 6.76-6.91 (m, 2 H), 7.03 (br. s., 1 H), 7.13 (s, 2 H), 7.30-7.37 (m, 2 H), 7.49 (d, J=2.0 Hz, 1 H), 7.92-8.03 (m, 1 H); LC/MS (electrospray+ve), m/z 526.2 (MH)$^+$, Retention time t=5.71 min; Purity: $UV_{220}$>98%, $UV_{254}$>98%; HRMS (ESI): m/z calcd for $C_{31}H_{31}N_3O_5$ [M+H]$^+$526.2351, found 526.2350.

Synthesis of 2-(3-((2,6-Dimethylphenylthio)methyl)-4-methoxyphenyl)-3-(furan-2-ylmethyl)-2,3-dihydroquinazolin-4(1H)-one (compound S2-8)

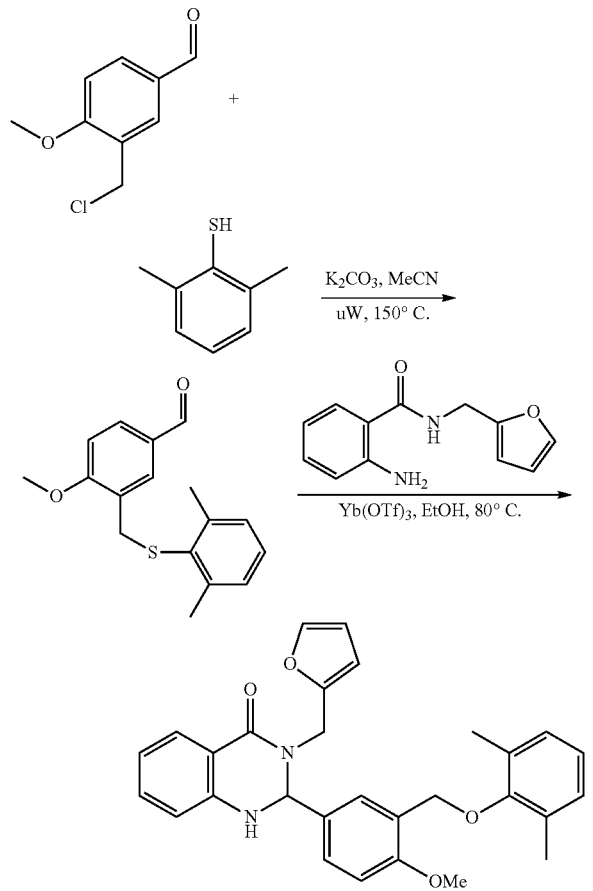

To a solution of 3-(chloromethyl)-4-methoxybenzaldehyde (91.0 mg, 0.5 mmol, 1.0 equiv) and 2,6-dimethylbenzenethiol (68.4 mg, 0.5 mmol, 1.0 equiv) in 4 mL acetonitrile was added potassium carbonate (0.55 g, 4.0 mmol, 8.0 equiv). The mixture was heated to 150° C. in the microwave for 10 min. After filtered off the solid and removed the solvent, 2-amino-N-(furan-2-ylmethyl)benzamide (107 mg, 0.5 mmol, 1.0 equiv) in 5 mL of EtOH was added followed by addition of Ytterbium trifluoromethanesulfonate (62 mg, 0.1 mmol, 0.2 equiv). The mixture was heated at 80° C. for 2 hours. Upon completion, the mixture was dried down and chromatographed on silica gel with 10-60% EtOAc/Hexanes gradient elution to give 2-(3-((2,6-dimethylphenylthio)methyl)-4-methoxyphenyl)-3-(furan-2-ylmethyl)-2,3-dihydroquinazolin-4(1H)-one (101.4 mg, 42%) as a white solid after triturating with diethyl ether. $^1$HNMR (400 MHz, DMSO-d$_6$) δ ppm 2.26 (s, 6 H), 3.56 (d, J=15.7 Hz, 1 H), 3.66 (s, 3 H), 3.72 (d, 1 H), 3.79 (d, 1 H), 5.12 (d, J=15.7 Hz, 1 H), 5.55 (d, J=2.2 Hz, 1 H), 6.25 (d, J=3.1 Hz, 1 H), 6.41 (dd, J=3.0, 1.9 Hz, 1 H), 6.59 (d, J=8.0 Hz, 1 H), 6.66 (t, J=7.5 Hz, 1 H), 6.78-6.94 (m, 2 H), 7.00-7.28 (m, 6 H), 7.59-7.66 (m, 2 H); LCMS: (electrospray+ve), m/z 485.2 (MH)$^+$, $t_R$=7.16 min, $UV_{254}$=98%. HRMS (ESI): m/z calcd for $C_{29}H_{28}N_2O_3S$ [M+H]$^+$485.1905, found 485.1905.

Synthesis of N-(4-(2-Methoxy-5-(4-oxo-3-(pyridin-3-ylmethyl)-1,2,3,4-tetrahydroquinazolin-2-yl)benzyloxy)-3,5-dimethylphenyl)acetamide (compound S2-17)

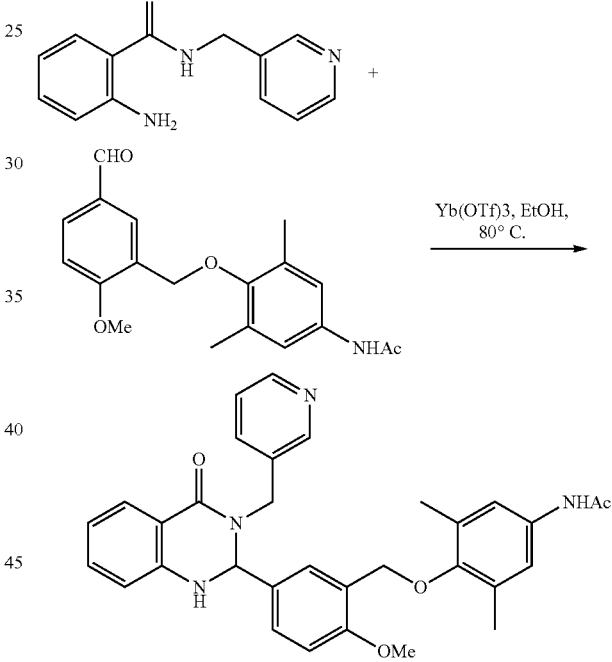

N-(4-(5-formyl-2-methoxybenzyloxy)-3,5-dimethylphenyl)acetamide (100 mg, 0.305 mmol), 2-amino-N-(pyridin-3-ylmethyl)benzamide (83 mg, 0.367 mmol), and 0.2 equiv of Yb(OTf)3 in 5 mL of EtOH were heated at 80° C. for 4 h. The reaction mixture was concentrated under reduced pressure and the residue was chromatographed on silica-gel using 2-40% Methanol in DCM to give the desired product N-(4-(2-methoxy-5-(4-oxo-3-(pyridin-3-ylmethyl)-1,2,3,4-tetrahydroquinazolin-2-yl)benzyloxy)-3,5-dimethylphenyl)acetamide (68.2 mg, 0.127 mmol, 41.6% yield) as a white solid. $^1$H NMR (400 MHz, DMSO-d$_6$) δ ppm 1.96 (s, 3 H), 2.08 (s, 6 H), 3.74 (s, 3 H), 3.98 (d, J=15.7 Hz, 1 H), 4.61 (s, 2 H), 5.07 (d, J=15.3 Hz, 1 H), 5.82 (d, J=2.3 Hz, 1 H), 6.58-6.74 (m, 2 H), 6.97 (d, J=8.2 Hz, 1 H), 7.12-7.37 (m, 6 H), 7.46 (d, J=2.0 Hz, 1 H), 7.64 (t, J=6.8 Hz, 2 H), 8.35-8.47 (m, 2 H), 9.67 (s, 1 H); LC/MS (electrospray+ve), m/z 537.2 (MH)$^+$, Retention time t=4.23 min; Purity: $UV_{220}$>98%, $UV_{254}$>98%; HRMS (ESI): m/z calcd for $C_{32}H_{32}N_4O_4$ [M+H]$^+$537.2511, found 537.2511.

Synthesis of N-(4-(2-methoxy-5-(3-(2-methoxyethyl)-4-oxo-1,2,3,4-tetrahydroquinazolin-2-yl)benzyloxy)-3,5-dimethylphenyl)acetamide (compound S2-29)

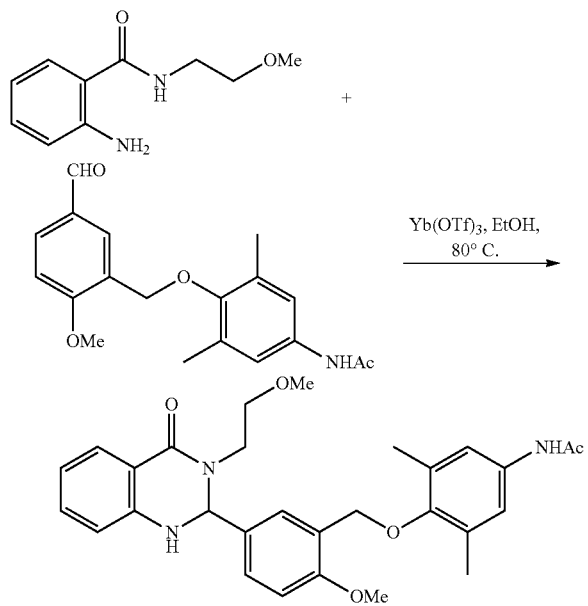

2-amino-N-(2-methoxyethyl)benzamide (71.2 mg, 0.367 mmol), N-(4-(5-formyl-2-methoxybenzyloxy)-3,5-dimethylphenyl)acetamide (100 mg, 0.305 mmol) and 0.2 equiv of Yb(OTf)3 in 5 mL of EtOH were heated at 80° C. for 2 h. The reaction mixture was concentrated under reduced pressure and the residue was chromatographed on silica-gel using 10-80% ethyl acetate in DCM to give the N-(4-(2-methoxy-5-(3-(2-methoxyethyl)-4-oxo-1,2,3,4-tetrahydroquinazolin-2-yl)benzyloxy)-3,5-dimethylphenyl)acetamide (77.9 mg, 0.155 mmol, 50.6% yield). $^1$H NMR (400 MHz, DMSO-d$_6$) δ ppm 1.97 (s, 3 H), 2.09 (s, 6 H), 2.90 (ddd, J=13.5, 6.7, 6.5 Hz, 1 H), 3.19 (s, 3 H), 3.31-3.53 (m, 2 H), 3.74 (s, 3 H), 3.86-4.06 (m, 1 H), 4.63 (s, 2 H), 5.85 (d, J=2.3 Hz, 1 H), 6.53-6.69 (m, 2 H), 6.98 (d, J=8.6 Hz, 1 H), 7.12-7.22 (m, 3 H), 7.22-7.31 (m, 2 H), 7.47 (d, J=2.3 Hz, 1 H), 7.61 (d, J=6.7 Hz, 1 H), 9.67 (s, 1 H); LC/MS (electrospray+ve), m/z 504.2 (MH)$^+$, Retention time t=5.27 min; Purity: $UV_{220}$>98%, $UV_{254}$>98%; HRMS (ESI): m/z calcd for $C_{29}H_{33}N_3O_5$ [M+H]$^+$504.2496, found 504.2498.

Culture of HEK-EM 293 cell lines and transient transfection. HEK-EM 293 cells were grown in Dulbecco's modified Eagle's Medium (DMEM) supplemented with 10% fetal bovine serum, 100 units/ml penicillin and 10 µg/ml streptomycin (Life Technologies Inc.) at 37° C. in a humidified 5% $CO_2$ incubator. The generation of a stable HEK-EM 293 cell line expressing TSHRs was described previously (Endocrinology 149, 5945, 2008). Cells were transiently transfected with wild-type TSHR or mutant receptors in 24-well plates ($7.5\times10^4$ cells per well) with 0.2 µg DNA/well using FuGENE™ 6 reagent (Roche) according to the manufacturer's protocol.

Culture of primary human thyrocytes. Thyroid tissue samples were collected from normal thyroid tissue from patients undergoing total thyroidectomy for thyroid cancer at the National Institutes of Health Clinical Center as described previously (Proc Nat Acad Sci 106, 12471, 2009). In brief, surgical specimens were maintained in Hanks Balanced Salt Solution (HBSS) on ice, minced into small pieces and digested with 3 mg/ml Collagenase Type IV (Gibco). Monodispersed cells were plated in 10 ml DMEM with 10% FBS in 10 cm tissue culture dishes, incubated at 37° C. in a humidified 5% $CO_2$ incubator and after 24 h the primary cultures of adherent thyroid cells were obtained. For determination of thyroglobulin (TG), thyroid peroxidase (TPO), TSHR or deiodinase type 2 (DIO2) mRNA expression, thyrocytes were seeded into 24-well plates at a density of $0.6\times10^4$ cells/well. After 24 h, the cells were washed with DMEM with 2% FBS and incubated in medium with 2 mM IBMX for 48 hr. The incubation was terminated by washing the cells with HBSS and adding lysis buffer.

Site-directed mutagenesis of TSHR. S281N, M453T, I568T and F631I mutations were introduced into wild-type TSHR-pcDNA3.1 via the QuickChange XL Site-Directed Mutagenesis kit (Stratagene). The constructs were verified by sequencing (MWG Biotech).

Determination of cAMP production. Transiently transfected HEK-EM293 cells or cells stably expressing TSHRs were seeded into 96-well plates at a density of 70,000 cells/well in DMEM containing 10% fetal bovine serum (FBS). Cells were cultured for 24 h before incubation for 20 to 40 min in HBSS/HEPES, pH 7.4 and then in HBSS/HEPES containing 1 mM 3-isobutyl-1-methylxanthine (IBMX) (SIGMA) without (basal) or with TSH or 1 in a humidified incubator at 37° C.; the levels of cAMP in cells incubated in HBSS/HEPES without IBMX were subtracted. Following aspiration of the mediums, cells were lysed using lysis buffer of the cAMP-Screen Direct™ System (Applied Biosystems). The cAMP content of the cell lysate was determined using the method described in the manufacturer's protocol. The potencies ($EC_{50}$) of the ligands were obtained from dose response curves by data analysis with GraphPad Prism 4 for Windows.

Effect of 1 on $^{125}$I-TSH binding. HEK-EM293 cells stably expressing TSHRs were seeded into 24-well plates and grown to near confluency. Cell surface binding was measured by incubation in 0.25 ml binding buffer (HBSS containing 2.5% milk powder and 0.2% BSA) containing 60,000 cpm bovine $^{125}$I-TSH without or with xx µM 1 for 2 hr at RT; nonspecific binding was measured in the presence of 1.8 µM unlabeled bovine TSH. Cells were washed 3 times with 0.5 ml ice cold HBSS and lysed with 0.5 ml 0.4 N NaOH, and the cell-associated radioactivity counted in a gamma counter.

Quantitative RT-PCR. mRNA levels were measured using primers and probes were from Applied Biosystems. Quantitative RT-PCR results were normalized to GAPDH to correct for differences in RNA input.

Statistical analysis. Data are expressed as mean±SE. The data were analyzed by Student's t-test or One-Way Anova; P<0.05 was considered significant.

In view of the many possible embodiments to which the principles of the disclosed agents and methods may be applied, it should be recognized that the illustrated embodiments are only preferred examples and should not be taken as limiting the scope of the invention.

What is claimed is:

1. A compound, or a pharmaceutically acceptable salt or ester thereof, having a structure of:

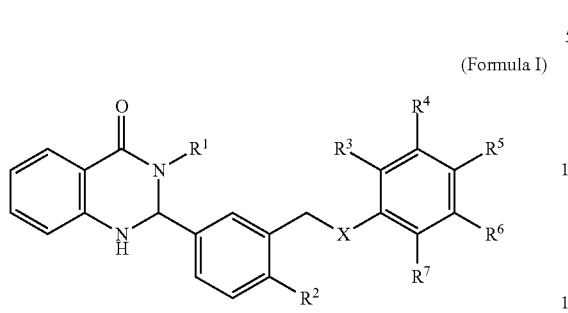

(Formula I)

wherein $R^1$ is selected from a furanyl-containing group, a pyridinyl-containing group, a thienyl-containing group, hydroxyalkyl, or alkoxyalkyl;

$R^2$ is H, alkoxy, alkyl, substituted alkyl or halogen; and $R^3$-$R^7$ are each individually selected from H, alkyl, substituted alkyl, or aminocarbonyl, provided that at least one of $R^3$ or $R^7$ is not H; and X is O or S; provided that the compound is not

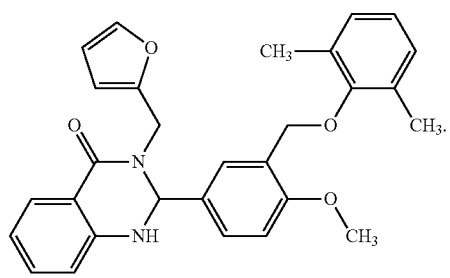 [SMILES: COc1ccc(C2Nc3ccccc3C(=O)N2Cc2ccco2)cc1COc1c(C)cccc1C]

2. The compound of claim 1, wherein $R^1$ is selected from furan-2-ylmethyl, pyridin-3-ylmethyl, thien-2-ylmethyl or methoxyethyl.

3. The compound of claim 1, wherein $R^2$ is methoxy.

4. The compound of claim 1, wherein $R^3$ and $R^7$ are each methyl.

5. The compound of claim 1, wherein X is O.

6. The compound of claim 1, wherein X is S.

7. The compound of claim 1, wherein $R^5$ is an aminocarbonyl group.

8. The compound of claim 1, wherein the compound is:

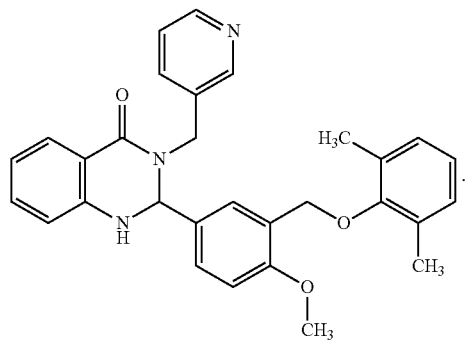 [SMILES: COc1ccc(C2Nc3ccccc3C(=O)N2Cc2cccnc2)cc1COc1c(C)cccc1C]

9. The compound of claim 1, wherein the compound is:

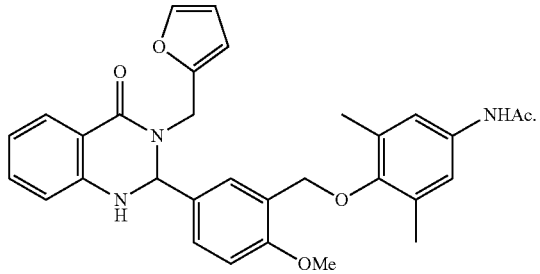 [SMILES: COc1ccc(C2Nc3ccccc3C(=O)N2Cc2ccco2)cc1COc1c(C)cc(NC(C)=O)cc1C]

10. The compound of claim 1, wherein the compound is:

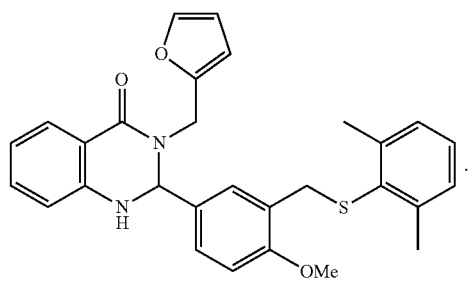 [SMILES: COc1ccc(C2Nc3ccccc3C(=O)N2Cc2ccco2)cc1CSc1c(C)cccc1C]

11. The compound of claim 1, wherein the compound is:

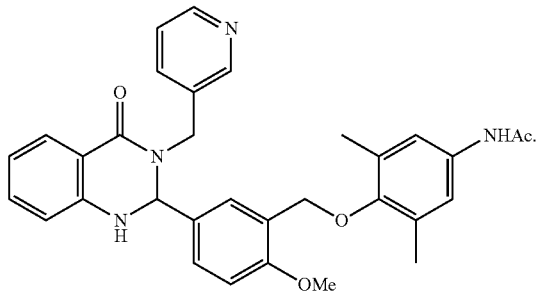 [SMILES: COc1ccc(C2Nc3ccccc3C(=O)N2Cc2cccnc2)cc1COc1c(C)cc(NC(C)=O)cc1C]

12. The compound of claim 1, wherein the compound is:

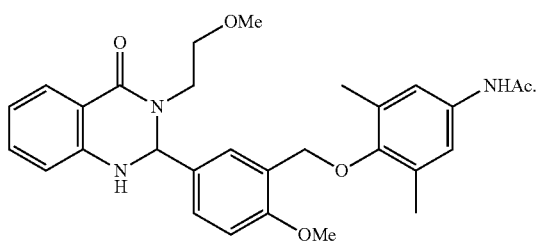 [SMILES: COCCN1C(=O)c2ccccc2NC1c1ccc(OC)c(COc2c(C)cc(NC(C)=O)cc2C)c1]

13. A compound, or a pharmaceutically acceptable salt thereof, having a structure of:

(Formula I)

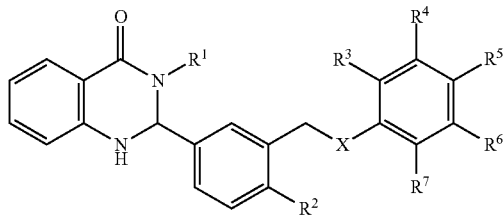

wherein $R^1$ is selected from a furanyl-containing group, a pyridinyl-containing group, a thienyl-containing group, hydroxyalkyl, or alkoxyalkyl;
$R^2$ is H, alkoxy, alkyl, substituted alkyl or halogen;
$R^3$ and $R^7$ are each individually alkyl;
$R^4$-$R^6$ are each individually selected from H, alkyl, substituted alkyl, halogen, or aminocarbonyl; and
X is O or S; provided that the compound is not

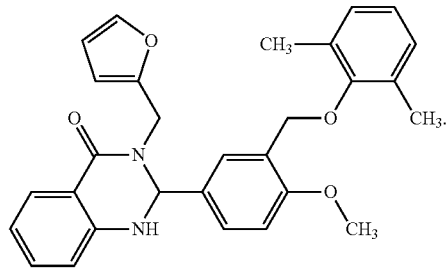 [SMILES: COc1ccc(C2Nc3ccccc3C(=O)N2Cc2ccco2)cc1COc1c(C)cccc1C]

14. The compound of claim 13, wherein $R^3$ and $R^7$ are each methyl.

15. A compound, or a pharmaceutically acceptable salt thereof, having a structure of:

(Formula I)

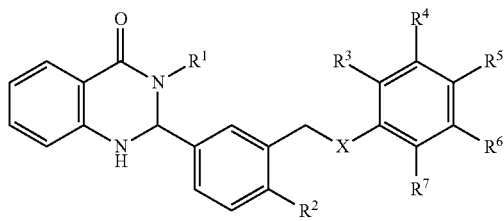

wherein $R^1$ is selected from a furanyl-containing group, a pyridinyl-containing group, a thienyl-containing group, hydroxyalkyl, or alkoxyalkyl;
$R^2$ is H, alkoxy, alkyl, substituted alkyl or halogen;
$R^3$, $R^4$, $R^6$ and $R^7$ are each individually selected from H, alkyl, substituted alkyl, halogen, or aminocarbonyl, provided that at least one of $R^3$ or $R^7$ is not H;
$R^5$ is aminocarbonyl; and
X is O or S.

16. The compound of claim 2, wherein $R^3$ and $R^7$ are each methyl.

17. The compound of claim 15, wherein $R^5$ is acetamido.

18. A pharmaceutical composition comprising at least one pharmaceutically acceptable additive and a therapeutically effective amount of at least one compound, or a pharmaceutically acceptable salt thereof, having a structure of:

(Formula I)

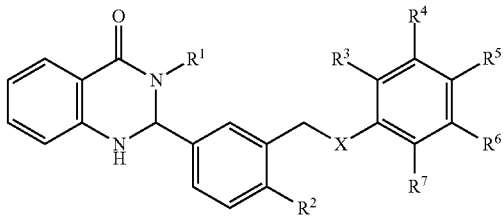

wherein $R^1$ is selected from a furanyl-containing group, a pyridinyl-containing group, a thienyl-containing group, hydroxyalkyl, or alkoxyalkyl;
$R^2$ is H, alkoxy, alkyl, substituted alkyl or halogen; and
$R^3$-$R^7$ are each individually selected from H, alkyl, substituted alkyl, halogen, or aminocarbonyl, provided that at least one of $R^3$ or $R^7$ is not H; and
X is O or S.

19. The pharmaceutical composition of claim 18, wherein $R^1$ is selected is selected from furan-2-ylmethyl, pyridin-3-ylmethyl, thien-2-ylmethyl or methoxyethyl.

20. The pharmaceutical composition of claim 18, $R^3$ and $R^7$ are each methyl.

21. A pharmaceutical composition comprising at least one pharmaceutically acceptable additive and a therapeutically effective amount of at least one compound, or a pharmaceutically acceptable salt or ester thereof, having a structure of:

(Formula II)

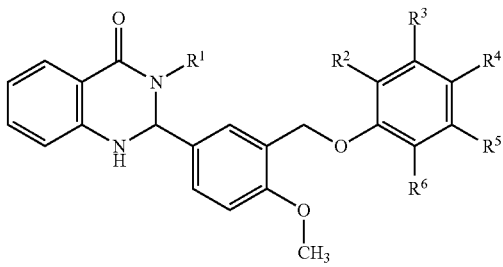

wherein $R^1$ is selected from:

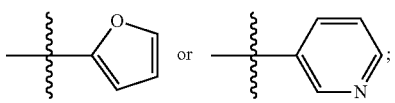 [SMILES: *c1ccco1 ; *c1cccnc1]

and
$R^2$-$R^6$ are each individually selected from H, alkyl, substituted alkyl or halogen.

22. The pharmaceutical composition of claim 21, wherein the compound is:

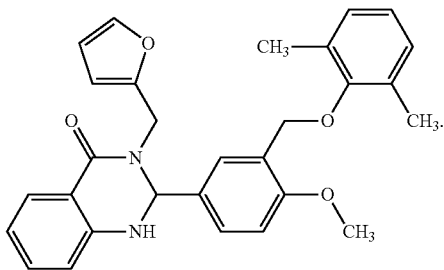 [SMILES: COc1ccc(C2Nc3ccccc3C(=O)N2Cc2ccco2)cc1COc1c(C)cccc1C]

23. The pharmaceutical composition of claim 21, wherein the compound is:

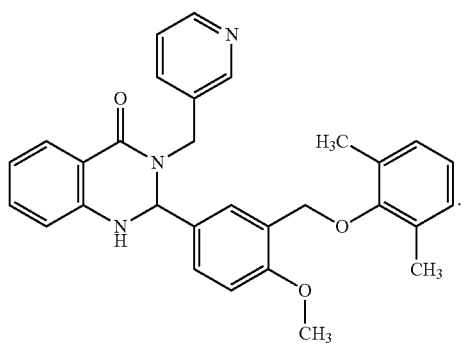 [SMILES: COc1ccc(C2Nc3ccccc3C(=O)N2Cc2cccnc2)cc1COc1c(C)cccc1C]

24. A method of treating Graves' disease in a subject, comprising administering to the subject an inverse agonist of TSHR or a neutral antagonist of TSHR.

25. The method of claim 24, wherein the inverse agonist of TSHR or the neutral antagonist of TSHR comprises a 2,3-dihydroquinazolin-4-one compound.

26. A method of treating Graves' disease in a subject, comprising administering to the subject a therapeutically effective amount of at least one compound, or a pharmaceutically acceptable salt thereof, having a structure of:

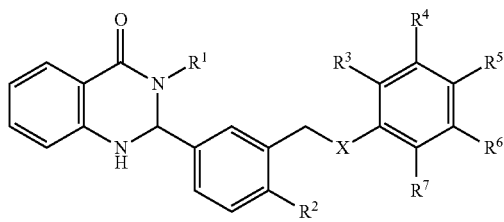

(Formula I)

wherein $R^1$ is selected from a furanyl-containing group, a pyridinyl-containing group, a thienyl-containing group, hydroxyalkyl, or alkoxyalkyl;
$R^2$ is H, alkoxy, alkyl, substituted alkyl or halogen; and
$R^3$-$R^7$ are each individually selected from H, alkyl, substituted alkyl, halogen, or aminocarbonyl; and
X is O or S.

27. The method of claim 24, wherein the Graves' disease is Graves' orbitopathy.

28. The method of claim 24, wherein the Graves' disease is Graves' hyperthyroidism.

29. The method of claim 28, wherein the Graves' hyperthyroidism is recurrent Graves' hyperthyroidism following radioiodine or anti-thyroid treatment.

30. A method for inhibiting signaling stimulated by thyroid-stimulating antibodies (TSAbs) in a subject, comprising administering to the subject a therapeutically effective amount of at least one compound, or a pharmaceutically acceptable salt thereof, having a structure of:

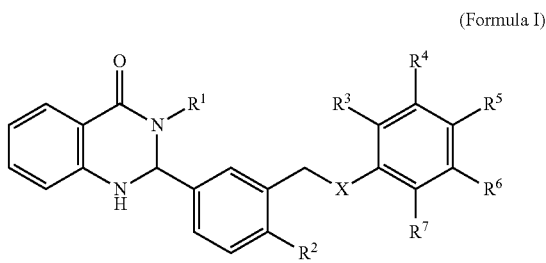

(Formula I)

wherein $R^1$ is selected from a furanyl-containing group, a pyridinyl-containing group, a thienyl-containing group, hydroxyalkyl, or alkoxyalkyl;
$R^2$ is H, alkoxy, alkyl, substituted alkyl or halogen; and
$R^3$-$R^7$ are each individually selected from H, alkyl, substituted alkyl, halogen, or aminocarbonyl; and
X is O or S.

31. The method of claim 30, wherein the method comprises inhibiting stimulation of the thyroid-stimulating hormone receptor by TSAbs in thyroid or retro-orbital cells.

32. A method of treating hyperthyroidism in a subject, comprising administering to the subject a therapeutically effective amount of at least one compound, or a pharmaceutically acceptable salt thereof, having a structure of:

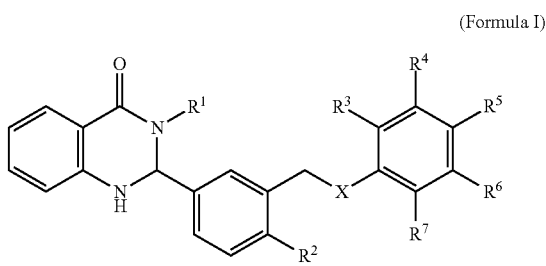

(Formula I)

wherein $R^1$ is selected from a furanyl-containing group, a pyridinyl-containing group, a thienyl-containing group, hydroxyalkyl, or alkoxyalkyl;
$R^2$ is H, alkoxy, alkyl, substituted alkyl or halogen; and
$R^3$-$R^7$ are each individually selected from H, alkyl, substituted alkyl, halogen, or aminocarbonyl; and
X is O or S.

33. A method of treating thyroid cancer in a subject, comprising administering to the subject a therapeutically effective amount of at least one compound, or a pharmaceutically acceptable salt thereof, having a structure of:

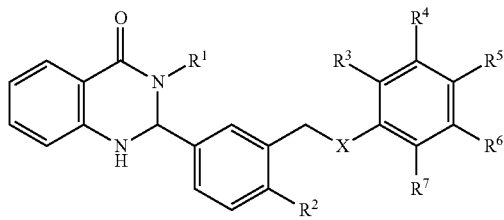

(Formula I)

wherein R[1] is selected from a furanyl-containing group, a pyridinyl-containing group, a thienyl-containing group, hydroxyalkyl, or alkoxyalkyl;

R[2] is H, alkoxy, alkyl, substituted alkyl or halogen; and

R[3]-R[7] are each individually selected from H, alkyl, substituted alkyl, halogen, or aminocarbonyl, provided that at least one of R[3] or R[7] is not H; and X is O or S.

34. The method of claim 33, wherein the method comprises administering the compound subsequent to thyroid cancer surgery or radioactive iodine therapy.

35. The method of claim 33, further comprising co-administering thyroid hormone therapy to the subject.

36. The method of claim 33, wherein the thyroid cancer is recurrent or metastatic thyroid cancer.

37. The method of claim 33, wherein administration of thyroid hormone is contraindicated in the subject.

38. The method of claim 36, wherein the thyroid cancer is recurrent despite suppression of the subject's endogenous thyroid-stimulating hormone.

39. The method of claim 36, wherein the thyroid cancer exhibits basal TSHR signaling activity and the compound inhibits such activity.

40. The method of claim 26, wherein R[1] is selected from furan-2-ylmethyl, pyridin-3-ylmethyl, thien-2-ylmethyl or methoxyethyl.

41. The method of claim 26, wherein R[2] is methoxy.

42. The method of claim 26, wherein R[3] and R[7] are each methyl.

43. The method of claim 26, wherein X is O.

44. The method of claim 26, wherein X is S.

45. The method of claim 26, R[5] is an aminocarbonyl group.

46. The method of claim 26, wherein the compound is:

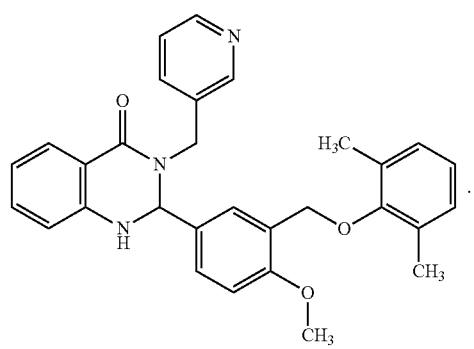 [SMILES: COc1ccc(C2Nc3ccccc3C(=O)N2Cc2cccnc2)cc1COc1c(C)cccc1C]

47. The method of claim 26, wherein the compound is:

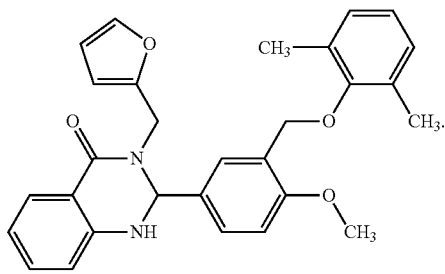 [SMILES: COc1ccc(C2Nc3ccccc3C(=O)N2Cc2ccco2)cc1COc1c(C)cccc1C]

48. The method of claim 16, wherein the compound is:

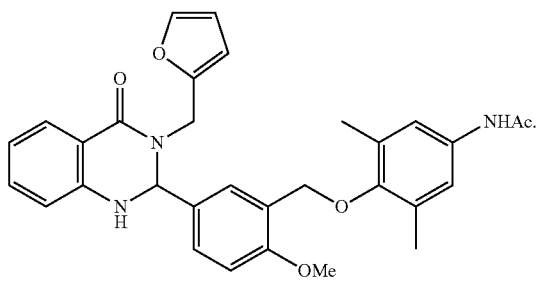 [SMILES: COc1ccc(C2Nc3ccccc3C(=O)N2Cc2ccco2)cc1COc1c(C)cc(NC(C)=O)cc1C]

49. The method of claim 26, wherein the compound is:

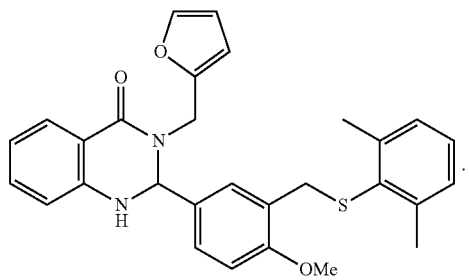 [SMILES: COc1ccc(C2Nc3ccccc3C(=O)N2Cc2ccco2)cc1CSc1c(C)cccc1C]

50. The method of claim 26, wherein the compound is:

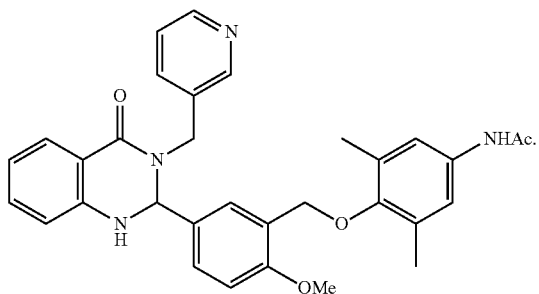 [SMILES: COc1ccc(C2Nc3ccccc3C(=O)N2Cc2cccnc2)cc1COc1c(C)cc(NC(C)=O)cc1C]

51. The method of claim 26, wherein the compound is:

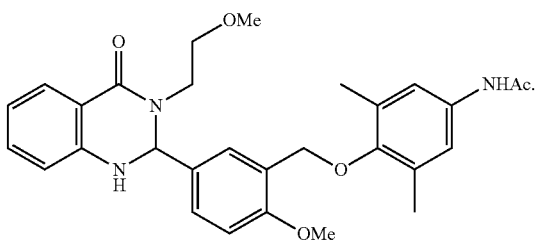 [SMILES: COCCN1C(=O)c2ccccc2NC1c1ccc(OC)c(COc2c(C)cc(NC(C)=O)cc2C)c1]

52. A method of treating thyroid cancer in a subject, comprising administering to the subject a therapeutically effective amount of at least one compound, or a pharmaceutically acceptable salt thereof, having a structure of:

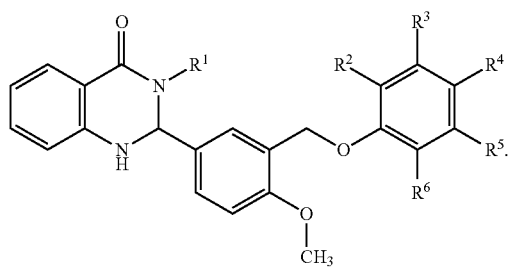

wherein $R^1$ is selected from:

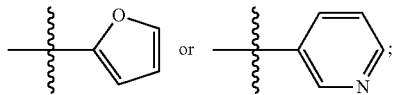 [SMILES: *c1ccco1 ; *c1cccnc1]

and $R^2$-$R^6$ are each individually selected from H, alkyl, substituted alkyl or halogen.

53. The method of claim 52, wherein the compound is:

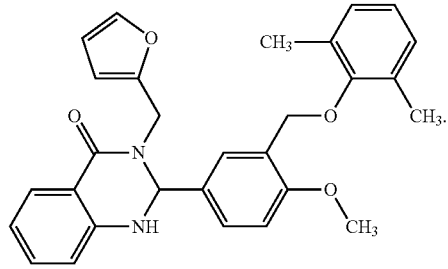 [SMILES: COc1ccc(C2Nc3ccccc3C(=O)N2Cc2ccco2)cc1COc1c(C)cccc1C]

54. The method of claim 52, wherein the compound is:

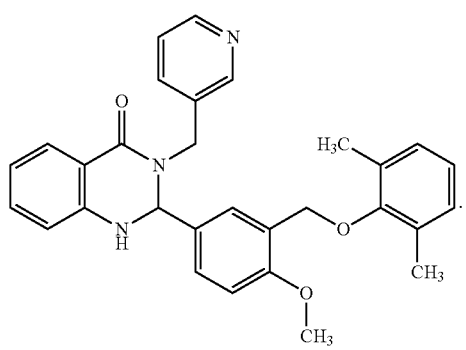 [SMILES: COc1ccc(C2Nc3ccccc3C(=O)N2Cc2cccnc2)cc1COc1c(C)cccc1C]

55. A method of treating hyperthyroidism in a subject, comprising administering to the subject a therapeutically effective amount of at least one compound, or a pharmaceutically acceptable salt thereof, having a structure of:

(Formula II)

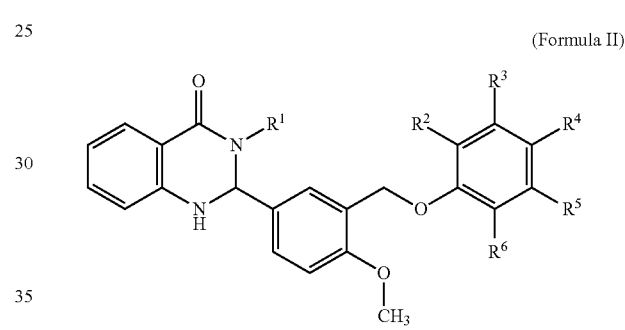

wherein $R^1$ is selected from:

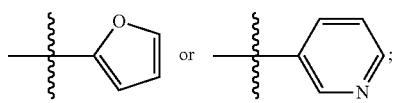 [SMILES: *c1ccco1 ; *c1cccnc1]

and $R^2$-$R^6$ are each individually selected from H, alkyl, substituted alkyl or halogen.

56. The method of claim 55, wherein the compound is:

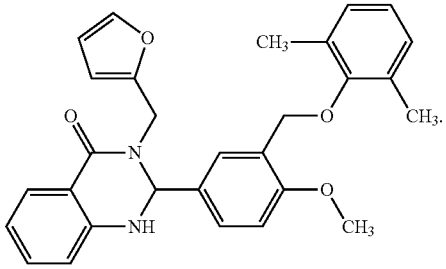 [SMILES: COc1ccc(C2Nc3ccccc3C(=O)N2Cc2ccco2)cc1COc1c(C)cccc1C]

57. The method of claim 55, wherein the compound is:

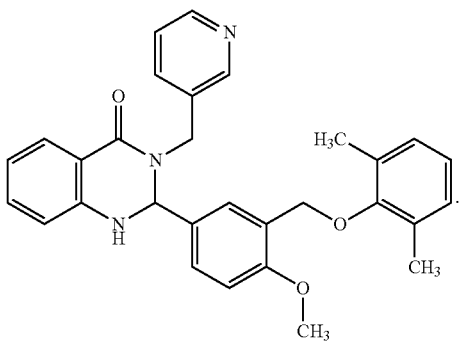 [SMILES: COc1ccc(C2Nc3ccccc3C(=O)N2Cc2cccnc2)cc1COc1c(C)cccc1C]

58. A method of treating Graves' disease in a subject, comprising administering to the subject a therapeutically effective amount of at least one compound, or a pharmaceutically acceptable salt or ester thereof, having a structure of:

(Formula II)

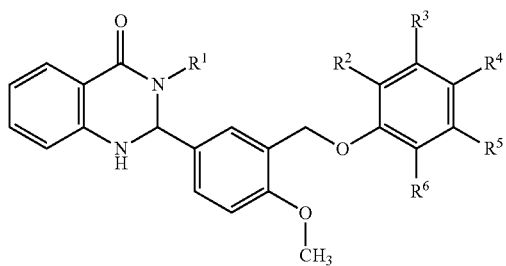

wherein $R^1$ is selected from:

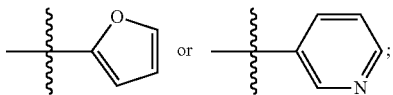

and $R^2$-$R^6$ are each individually selected from H, alkyl, substituted alkyl or halogen.

59. The method of claim 27, wherein the compound is:

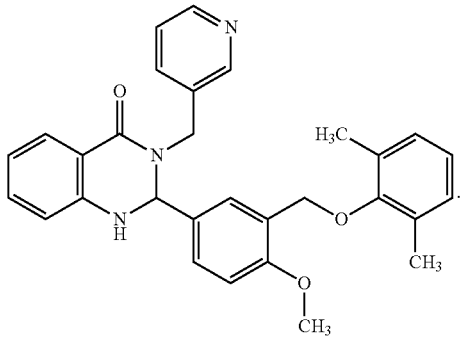

60. The method of claim 27, wherein $R^1$ is selected from furan-2-ylmethyl or pyridin-3-ylmethyl; $R^2$ is methoxy; and $R^3$ and $R^7$ are each methyl.

61. The method of claim 25, wherein the 2,3-dihydroquinazolin-4-one compound is a 2-substituted, 3-substituted 2,3-dihydroquinazolin-4-one compound, wherein the substituent at the 2-position is a furanyl-containing group, a pyridinyl-containing group, a thienyl-containing group, hydroxyalkyl, or alkoxyalkyl, and the substituent at the 3-position is —$Ar^1$—$CH_2$—X—$Ar^2$, wherein $Ar^1$ is a substituted or unsubstituted arylene group; $Ar^2$ is a substituted or unsubstituted aryl group; and X is O or S.

* * * * *